(12) United States Patent
Tirouvanziam et al.

(10) Patent No.: US 9,157,912 B2
(45) Date of Patent: *Oct. 13, 2015

(54) METHOD FOR THE DIAGNOSIS AND/OR PROGNOSIS OF GRANULOCYTE-RELATED INFLAMMATORY STATES

(75) Inventors: Rabindra Tirouvanziam, Redwood City, CA (US); Julie Laval, Caux (FR); Jean-Luc Battini, Montpellier (FR); Marc Sitbon, Montpellier (FR)

(73) Assignees: CENTRE NATIONAL DE LA RECHERCHE SCIENTIFIQUE, Paris (FR); UNIVERSITE MONTPELLIER 2 SCIENCES ET TECHNIQUES, Montpellier (FR); STANFORD UNIVERSITY, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/823,537

(22) PCT Filed: Sep. 19, 2011

(86) PCT No.: PCT/EP2011/066231
§ 371 (c)(1),
(2), (4) Date: Jun. 5, 2013

(87) PCT Pub. No.: WO2012/035166
PCT Pub. Date: Mar. 22, 2012

(65) Prior Publication Data
US 2013/0252251 A1    Sep. 26, 2013

Related U.S. Application Data

(63) Continuation of application No. PCT/IB2010/002624, filed on Sep. 17, 2010.

(51) Int. Cl.
G01N 33/566    (2006.01)
G01N 33/564    (2006.01)
G01N 33/569    (2006.01)
G01N 33/68     (2006.01)

(52) U.S. Cl.
CPC ............ *G01N 33/566* (2013.01); *G01N 33/564* (2013.01); *G01N 33/56972* (2013.01); *G01N 33/6872* (2013.01); *G01N 33/6893* (2013.01); *G01N 2800/122* (2013.01); *G01N 2800/24* (2013.01); *G01N 2800/382* (2013.01)

(58) Field of Classification Search
None
See application file for complete search history.

(56) References Cited

U.S. PATENT DOCUMENTS

2004/0176314 A1    9/2004    Beseme et al.

FOREIGN PATENT DOCUMENTS

| WO | 01/31021      | 5/2001  |
| WO | 03/092582     | 11/2003 |
| WO | 2004/096841   | 11/2004 |
| WO | 2005/095442   | 10/2005 |
| WO | 2010/079208   | 7/2010  |

OTHER PUBLICATIONS

Manel N, et al. Frontiers in Bioscience, 9:3218-3241, 2004.*
International Search Report dated Nov. 3, 2011 in corresponding PCT application.
Lavanya Madakasira et al: "Cell surface expression of the bovine leukemia virus-binding receptor on B and T lymphocytes is induced by receptor engagement", Journal of Immunology, American Association of Immunologists, US, vol. 181, No. 2, Jul. 15, 2008, pp. 891-898.

* cited by examiner

*Primary Examiner* — Robert Landsman
(74) *Attorney, Agent, or Firm* — Young & Thompson

(57) ABSTRACT

A method for the diagnosis and/or prognosis of inflammatory states, and the use of at least one soluble receptor-binding (RBD), for the identification and quantification of the expression of membrane receptors present on the surface of target granulocytes, said identification and quantification taking place at a given time or during a given time interval, and allowing the diagnosis and/or prognosis of inflammatory states in a mammal.

17 Claims, 5 Drawing Sheets

SEQUENCE LISTING

<160> NUMBER OF SEQ ID NOS: 31

<210> SEQ ID NO 1
<211> LENGTH: 328
<212> TYPE: PRT
<213> ORGANISM: Artificial Sequence
<220> FEATURE:
<223> OTHER INFORMATION: Derived from Env Amphotropic Murine Leukaemia
      Virus 4070A

<220> FEATURE:
<221> NAME/KEY: PEPTIDE
<222> LOCATION: (1)..(328)

<400> SEQUENCE: 1

Met Ala Arg Ser Thr Leu Ser Lys Pro Pro Gln Asp Lys Ile Asn Pro
1               5                   10                  15

Trp Lys Pro Leu Ile Val Met Gly Val Leu Gly Val Gly Met Ala
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
50                  55                  60

Asp Ala Phe Pro Lys Leu Tyr Phe Asp Leu Cys Asp Leu Val Gly Glu
65              70                  75                  80

Glu Trp Asp Pro Ser Asp Gln Glu Pro Tyr Val Gly Tyr Gly Cys Lys
                85                  90                  95

Tyr Pro Ala Gly Arg Gln Arg Thr Arg Thr Phe Asp Phe Tyr Val Cys
            100                 105                 110

Pro Gly His Thr Val Lys Ser Gly Cys Gly Gly Pro Gly Glu Gly Tyr
        115                 120                 125

Cys Gly Lys Trp Gly Cys Glu Thr Thr Gly Gln Ala Tyr Trp Lys Pro
130                 135                 140

Thr Ser Ser Trp Asp Leu Ile Ser Leu Lys Arg Gly Asn Thr Pro Trp
145                 150                 155                 160

Asp Thr Gly Cys Ser Lys Val Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
        195                 200                 205

Gly Pro Lys Ser Trp Gly Leu Arg Leu Tyr Arg Thr Gly Thr Asp Pro
210                 215                 220

Ile Thr Met Phe Ser Leu Thr Arg Gln Val Leu Asn Val Gly Pro Arg
225                 230                 235                 240

Val Pro Ile Gly Pro Asn Pro Val Leu Pro Asp Gln Arg Leu Pro Ser
                245                 250                 255

Ser Pro Ile Glu Ile Val Pro Ala Pro Gln Pro Ser Pro Leu Asn
            260                 265                 270

Thr Ser Tyr Pro Pro Ser Thr Thr Ser Thr Pro Ser Thr Ser Pro Thr
        275                 280                 285

Ser Pro Ser Val Pro Gln Pro Pro Gly Thr Gly Asp Arg Leu Leu
290                 295                 300

Ala Leu Val Lys Gly Ala Tyr Gln Ala Leu Asn Leu Thr Asn Pro Asp
305                 310                 315                 320

Lys Thr Gln Glu Cys Trp Leu Cys
                325

<210> SEQ ID NO 2
<211> LENGTH: 357
<212> TYPE: PRT
<213> ORGANISM: Artificial Sequence
<220> FEATURE:
<223> OTHER INFORMATION: Derived from Env Gibbon Ape Leukaemia Virus
<220> FEATURE:
<221> NAME/KEY: PEPTIDE
<222> LOCATION: (1)..(357)

<400> SEQUENCE: 2

```
Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
            20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Ser Lys Arg Val Arg Pro
                100                 105                 110

Pro Asp Ser Asp Tyr Thr Ala Ala Tyr Lys Gln Ile Thr Trp Gly Ala
            115                 120                 125

Ile Gly Cys Ser Tyr Pro Arg Ala Arg Thr Arg Met Ala Ser Ser Thr
130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
        195                 200                 205

His Gln Thr Gly Trp Cys Asn Pro Leu Lys Ile Asp Phe Thr Asp Lys
    210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys
                245                 250                 255

Ile Thr Asn Met Pro Ala Val Ala Val Gly Pro Asp Leu Val Leu Val
            260                 265                 270

Glu Gln Gly Pro Pro Arg Thr Ser Leu Ala Leu Pro Pro Pro Leu Pro
        275                 280                 285

Pro Arg Glu Ala Pro Pro Ser Leu Pro Asp Ser Asn Ser Thr Ala
    290                 295                 300

Leu Ala Thr Ser Ala Gln Thr Pro Thr Val Arg Lys Thr Ile Val Thr
305                 310                 315                 320

Leu Asn Thr Pro Pro Pro Thr Thr Gly Asp Arg Leu Phe Asp Leu Val
                325                 330                 335

Gln Gly Ala Phe Leu Thr Leu Asn Ala Thr Asn Pro Gly Ala Thr Glu
            340                 345                 350

Ser Cys Trp Leu Cys
        355
```

<210> SEQ ID NO 3
<211> LENGTH: 239
<212> TYPE: PRT
<213> ORGANISM: Artificial Sequence
<220> FEATURE:
<223> OTHER INFORMATION: Derived from Env Feline endogenous Leukaemia
    Virus RD 114

-continued

```
<220> FEATURE:
<221> NAME/KEY: PEPTIDE
<222> LOCATION: (1)..(239)

<400> SEQUENCE: 3

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
                20                  25                  30

Gln His Gly Lys Pro Cys Glu Cys Ser Gly Gly Gln Val Ser Glu Ala
            35                  40                  45

Pro Pro Asn Ser Ile Gln Gln Val Thr Cys Pro Gly Lys Thr Ala Tyr
    50                  55                  60

Leu Met Thr Asn Gln Lys Trp Lys Cys Arg Val Thr Pro Lys Ile Ser
65                  70                  75                  80

Pro Ser Gly Gly Glu Leu Gln Asn Cys Pro Cys Asn Thr Phe Gln Asp
                85                  90                  95

Ser Met His Ser Ser Cys Tyr Thr Glu Tyr Arg Gln Cys Arg Arg Ile
                100                 105                 110

Asn Lys Thr Tyr Tyr Thr Ala Thr Leu Leu Lys Ile Arg Ser Gly Ser
            115                 120                 125

Leu Asn Glu Val Gln Ile Leu Gln Asn Pro Asn Gln Leu Leu Gln Ser
    130                 135                 140

Pro Cys Arg Gly Ser Ile Asn Gln Pro Val Cys Trp Ser Ala Thr Ala
145                 150                 155                 160

Pro Ile His Ile Ser Asp Gly Gly Pro Leu Asp Thr Lys Arg Val
                165                 170                 175

Trp Thr Val Gln Lys Arg Leu Glu Gln Ile His Lys Ala Met Thr Pro
                180                 185                 190

Glu Leu Gln Tyr His Pro Leu Ala Leu Pro Lys Val Arg Asp Asp Leu
            195                 200                 205

Ser Leu Asp Ala Arg Thr Phe Asp Ile Leu Asn Thr Thr Phe Arg Leu
    210                 215                 220

Leu Gln Met Ser Asn Phe Ser Leu Ala Gln Asp Cys Trp Leu Cys
225                 230                 235

<210> SEQ ID NO 4
<211> LENGTH: 462
<212> TYPE: PRT
<213> ORGANISM: Artificial Sequence
<220> FEATURE:
<223> OTHER INFORMATION: Derived from Vesicular Stomatitis Virus G
      glycoprotein
<220> FEATURE:
<221> NAME/KEY: PEPTIDE
<222> LOCATION: (1)..(462)

<400> SEQUENCE: 4

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
                20                  25                  30

Val Pro Ser Asn Tyr His Tyr Cys Pro Ser Ser Ser Asp Leu Asn Trp
            35                  40                  45

His Asn Asp Leu Ile Gly Thr Ala Ile Gln Val Lys Met Pro Lys Ser
    50                  55                  60

His Lys Ala Ile Gln Ala Asp Gly Trp Met Cys His Ala Ser Lys Trp
65                  70                  75                  80
```

Val Thr Thr Cys Asp Phe Arg Trp Tyr Gly Pro Lys Tyr Ile Thr Gln
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Val Ile Val Gln
            130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                165                 170                 175

Val His Asn Ser Thr Thr Trp His Ser Asp Tyr Lys Val Lys Gly Leu
            180                 185                 190

Cys Asp Ser Asn Leu Ile Ser Met Asp Ile Thr Phe Phe Ser Glu Asp
            195                 200                 205

Gly Glu Leu Ser Ser Leu Gly Lys Glu Gly Thr Gly Phe Arg Ser Asn
210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                245                 250                 255

Asp Lys Asp Leu Phe Ala Ala Ala Arg Phe Pro Glu Cys Pro Glu Gly
            260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
            290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                325                 330                 335

Gly Thr Leu Lys Tyr Phe Glu Thr Arg Tyr Ile Arg Val Asp Ile Ala
            340                 345                 350

Ala Pro Ile Leu Ser Arg Met Val Gly Met Ile Ser Gly Thr Thr Thr
            355                 360                 365

Glu Arg Glu Leu Trp Asp Asp Trp Ala Pro Tyr Glu Asp Val Glu Ile
            370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                405                 410                 415

Lys Ala Gln Val Phe Glu His Pro His Ile Gln Asp Ala Ala Ser Gln
            420                 425                 430

Leu Pro Asp Asp Glu Ser Leu Phe Phe Gly Asp Thr Gly Leu Ser Lys
            435                 440                 445

Asn Pro Ile Glu Leu Val Glu Gly Trp Phe Ser Ser Trp Lys
            450                 455                 460

<210> SEQ ID NO 5
<211> LENGTH: 339
<212> TYPE: PRT
<213> ORGANISM: Artificial Sequence
<220> FEATURE:
<223> OTHER INFORMATION: Derived from Env ecotropic Moloney -Murine
      Leukaemia Virus
<220> FEATURE:
<221> NAME/KEY: PEPTIDE
<222> LOCATION: (1)..(339)

<400> SEQUENCE: 5

```
Met Ala Arg Ser Thr Leu Ser Lys Pro Leu Lys Asn Lys Val Asn Pro
1               5                   10                  15

Arg Gly Pro Leu Ile Pro Leu Ile Leu Met Leu Arg Gly Val Ser
            20                  25                  30

Thr Ala Ser Pro Gly Ser Ser Pro His Gln Val Tyr Asn Ile Thr Trp
            35                  40                  45

Glu Val Thr Asn Gly Asp Arg Glu Thr Val Trp Ala Thr Ser Gly Asn
50                  55                  60

His Pro Leu Trp Thr Trp Trp Pro Asp Leu Thr Pro Asp Leu Cys Met
65                  70                  75                  80

Leu Ala His His Gly Pro Ser Tyr Trp Gly Leu Glu Tyr Gln Ser Pro
                85                  90                  95

Phe Ser Ser Pro Pro Gly Pro Cys Cys Ser Gly Gly Ser Ser Pro
            100                 105                 110

Gly Cys Ser Arg Asp Cys Glu Glu Pro Leu Thr Ser Leu Thr Pro Arg
            115                 120                 125

Cys Asn Thr Ala Trp Asn Arg Leu Lys Leu Asp Gln Thr Thr His Lys
130                 135                 140

Ser Asn Glu Gly Phe Tyr Val Cys Pro Gly Pro His Arg Pro Arg Glu
145                 150                 155                 160

Ser Lys Ser Cys Gly Gly Pro Asp Ser Phe Tyr Cys Ala Tyr Trp Gly
                165                 170                 175

Cys Glu Thr Thr Gly Arg Ala Tyr Trp Lys Pro Ser Ser Ser Trp Asp
            180                 185                 190

Phe Ile Thr Val Asn Asn Asn Leu Thr Ser Asp Gln Ala Val Gln Val
            195                 200                 205

Cys Lys Asp Asn Lys Trp Cys Asn Pro Leu Val Ile Arg Phe Thr Asp
210                 215                 220

Ala Gly Arg Arg Val Thr Ser Trp Thr Thr Gly His Tyr Trp Gly Leu
225                 230                 235                 240

Arg Leu Tyr Val Ser Gly Gln Asp Pro Gly Leu Thr Phe Gly Ile Arg
                245                 250                 255

Leu Arg Tyr Gln Asn Leu Gly Pro Arg Val Pro Ile Gly Pro Asn Pro
            260                 265                 270

Val Leu Ala Asp Gln Gln Pro Leu Ser Lys Pro Lys Pro Val Lys Ser
            275                 280                 285

Pro Ser Val Thr Lys Pro Pro Ser Gly Thr Pro Leu Ser Pro Thr Gln
290                 295                 300

Leu Pro Pro Ala Gly Thr Glu Asn Arg Leu Leu Asn Leu Val Asp Gly
305                 310                 315                 320

Ala Tyr Gln Ala Leu Asn Leu Thr Ser Pro Asp Lys Thr Gln Glu Cys
                325                 330                 335

Trp Leu Cys
```

<210> SEQ ID NO 6
<211> LENGTH: 349
<212> TYPE: PRT
<213> ORGANISM: Artificial Sequence

```
<220> FEATURE:
<223> OTHER INFORMATION: Derived from Env ecotropic Friend Murine
      Leukaemia Virus
<220> FEATURE:
<221> NAME/KEY: PEPTIDE
<222> LOCATION: (1)..(349)

<400> SEQUENCE: 6
```

Met Ala Cys Ser Thr Leu Pro Lys Ser Pro Lys Asp Lys Ile Asp Pro
1               5                   10                  15

Arg Asp Leu Leu Ile Pro Leu Ile Leu Phe Leu Ser Leu Lys Gly Ala
                20                  25                  30

Arg Ser Ala Ala Pro Gly Ser Ser Pro His Gln Val Tyr Asn Ile Thr
            35                  40                  45

Trp Glu Val Thr Asn Gly Asp Arg Glu Thr Val Trp Ala Ile Ser Gly
        50                  55                  60

Asn His Pro Leu Trp Thr Trp Trp Pro Val Leu Thr Pro Asp Leu Cys
65                  70                  75                  80

Met Leu Ala Leu Ser Gly Pro Pro His Trp Gly Leu Glu Tyr Gln Ala
                85                  90                  95

Pro Tyr Ser Ser Pro Pro Gly Pro Pro Cys Cys Ser Gly Ser Ser Gly
                100                 105                 110

Ser Ser Ala Gly Cys Ser Arg Asp Cys Asp Glu Pro Leu Thr Ser Leu
            115                 120                 125

Thr Pro Arg Cys Asn Thr Ala Trp Asn Arg Leu Lys Leu Asp Gln Val
        130                 135                 140

Thr His Lys Ser Ser Glu Gly Phe Tyr Val Cys Pro Gly Ser His Arg
145                 150                 155                 160

Pro Arg Glu Ala Lys Ser Cys Gly Gly Pro Asp Ser Phe Tyr Cys Ala
                165                 170                 175

Ser Trp Gly Cys Glu Thr Thr Gly Arg Val Tyr Trp Lys Pro Ser Ser
                180                 185                 190

Ser Trp Asp Tyr Ile Thr Val Asp Asn Asn Leu Thr Thr Ser Gln Ala
            195                 200                 205

Val Gln Val Cys Lys Asp Asn Lys Trp Cys Asn Pro Leu Ala Ile Gln
        210                 215                 220

Phe Thr Asn Ala Gly Lys Gln Val Thr Ser Trp Thr Thr Gly His Tyr
225                 230                 235                 240

Trp Gly Leu Arg Leu Tyr Val Ser Gly Arg Asp Pro Gly Leu Thr Phe
                245                 250                 255

Gly Ile Arg Leu Arg Tyr Gln Asn Leu Gly Pro Arg Val Pro Ile Gly
                260                 265                 270

Pro Asn Pro Val Leu Ala Asp Gln Leu Ser Leu Pro Arg Pro Asn Pro
            275                 280                 285

Leu Pro Lys Pro Ala Lys Ser Pro Pro Ala Ser Asn Ser Thr Pro Thr
        290                 295                 300

Leu Ile Ser Pro Ser Pro Thr Pro Thr Gln Pro Pro Ala Gly Thr
305                 310                 315                 320

Gly Asp Arg Leu Leu Asn Leu Val Gln Gly Ala Tyr Gln Ala Leu Asn
                325                 330                 335

Leu Thr Asn Pro Asp Lys Thr Gln Glu Cys Trp Leu Cys
                340                 345

```
<210> SEQ ID NO 7
<211> LENGTH: 340
<212> TYPE: PRT
<213> ORGANISM: Artificial Sequence
<220> FEATURE:
<223> OTHER INFORMATION: Derived from Env ecotropic AKV Murine Leukaemia
      Virus
<220> FEATURE:
<221> NAME/KEY: PEPTIDE
<222> LOCATION: (1)..(340)

<400> SEQUENCE: 7

Met Glu Ser Thr Thr Leu Ser Lys Pro Phe Lys Asn Gln Val Asn Pro
1               5                   10                  15

Trp Gly Pro Leu Ile Val Leu Leu Ile Leu Gly Gly Val Asn Pro Val
            20                  25                  30

Thr Leu Gly Asn Ser Pro His Gln Val Phe Asn Leu Thr Trp Glu Val
        35                  40                  45

Thr Asn Gly Asp Arg Glu Thr Val Trp Ala Ile Thr Gly Asn His Pro
    50                  55                  60

Leu Trp Thr Trp Trp Pro Asp Leu Thr Pro Asp Leu Cys Met Leu Ala
65                  70                  75                  80

Leu His Gly Pro Ser Tyr Trp Gly Leu Glu Tyr Arg Ala Pro Phe Ser
                85                  90                  95

Pro Pro Pro Gly Pro Pro Cys Cys Ser Gly Ser Ser Asp Ser Thr Pro
            100                 105                 110

Gly Cys Ser Arg Asp Cys Glu Glu Pro Leu Thr Ser Tyr Thr Pro Arg
        115                 120                 125

Cys Asn Thr Ala Trp Asn Arg Leu Lys Leu Ser Lys Val Thr His Ala
130                 135                 140

His Asn Gly Gly Phe Tyr Val Cys Pro Gly Pro His Arg Pro Arg Trp
145                 150                 155                 160

Ala Arg Ser Cys Gly Gly Pro Glu Ser Phe Tyr Cys Ala Ser Trp Gly
                165                 170                 175

Cys Glu Thr Thr Gly Arg Ala Ser Trp Lys Pro Ser Ser Ser Trp Asp
            180                 185                 190

Tyr Ile Thr Val Ser Asn Asn Leu Thr Ser Asp Gln Ala Thr Pro Val
        195                 200                 205

Cys Lys Gly Asn Glu Trp Cys Asn Ser Leu Thr Ile Arg Phe Thr Ser
210                 215                 220

Phe Gly Lys Gln Ala Thr Ser Trp Val Thr Gly His Trp Trp Gly Leu
225                 230                 235                 240

Arg Leu Tyr Val Ser Gly His Asp Pro Gly Leu Ile Phe Gly Ile Arg
                245                 250                 255

Leu Lys Ile Thr Asp Ser Gly Pro Arg Val Pro Ile Gly Pro Asn Pro
            260                 265                 270

Val Leu Ser Asp Arg Arg Pro Pro Ser Arg Pro Arg Pro Thr Arg Ser
        275                 280                 285

Pro Pro Pro Ser Asn Ser Thr Pro Thr Glu Thr Pro Leu Thr Leu Pro
290                 295                 300

Glu Pro Pro Pro Ala Gly Val Glu Asn Arg Leu Leu Asn Leu Val Lys
305                 310                 315                 320

Gly Ala Tyr Gln Ala Leu Asn Leu Thr Ser Pro Asp Lys Thr Gln Glu
                325                 330                 335

Cys Trp Leu Cys
            340
```

-continued

```
<210> SEQ ID NO 8
<211> LENGTH: 289
<212> TYPE: PRT
<213> ORGANISM: Artificial Sequence
<220> FEATURE:
<223> OTHER INFORMATION: Derived from Env M813 Murine Leukaemia Virus
<220> FEATURE:
<221> NAME/KEY: PEPTIDE
<222> LOCATION: (1)..(289)

<400> SEQUENCE: 8

Met Ala Asp Ser Ser Leu Ser Glu Pro Ser Lys Asp Lys Thr His Ser
1               5                   10                  15

Arg Ala Pro Thr Ile Ala Leu Gly Ile Leu Val Leu Gly Arg Val
            20                  25                  30

Ala Gln Gly Gly Ser Pro His Gln Pro Val Thr Leu Thr Trp Gln Val
        35                  40                  45

Leu Asp Glu Glu Leu Tyr Val Lys Trp Glu Thr Ser Gly Lys His Pro
    50                  55                  60

Glu Trp Thr Trp Trp Pro Asp Leu Thr Pro Asp Leu Ser Gly Phe Ser
65                  70                  75                  80

Cys Asp Tyr Ser Gln Leu Asn Val Pro Asp Phe Tyr Val Cys Pro Gly
                85                  90                  95

His Gly Lys Ser Tyr Ser Arg Arg Val Cys Gly Gly Ala Glu Ser Ala
            100                 105                 110

Phe Cys Ala Lys Trp Gly Cys Glu Thr Thr Gly Asp Ala Tyr Trp Asn
        115                 120                 125

Pro Asn Arg Pro Asp Leu Ile Ile Val Lys Lys Gly Gln Asn Arg Thr
    130                 135                 140

Ala Cys Lys Gly Asn Lys Cys Gln Gly Lys Tyr Cys Asn Pro Leu Lys
145                 150                 155                 160

Ile Thr Phe Thr Asp Gln Gly Lys Asn Ser Arg Glu Trp Lys Arg Gly
                165                 170                 175

Leu Arg Trp Gly Cys Trp Val His Leu Leu Ser Gln His Phe Ile Phe
            180                 185                 190

Tyr Ile Arg Leu Gln Val Thr Arg Ser Pro Val Leu Ala Ile Gly Pro
        195                 200                 205

Asn Pro Val Val Ala Asp Gln Lys Pro Pro Ser Arg Pro Ala Pro Val
    210                 215                 220

Ile Pro Pro Val Pro Pro Gln Val Asn Pro Thr Gly Ala Thr Asp Asn
225                 230                 235                 240

Thr Thr Gly Thr Thr Pro Thr Thr Val Leu Ser Thr Lys Gln Pro Gln
                245                 250                 255

Arg Pro Gly Thr Gly Asp Arg Leu Leu Asp Leu Val Gln Gly Ala Tyr
            260                 265                 270

Leu Ala Leu Asn Phe Thr Asn Pro Glu Lys Thr Gln Glu Cys Trp Leu
        275                 280                 285

Cys

<210> SEQ ID NO 9
<211> LENGTH: 319
<212> TYPE: PRT
<213> ORGANISM: Artificial Sequence
<220> FEATURE:
<223> OTHER INFORMATION: Derived from Env 10A1 Murine Leukaemia Virus
<220> FEATURE:
<221> NAME/KEY: PEPTIDE
<222> LOCATION: (1)..(319)
```

<400> SEQUENCE: 9

```
Met Glu Gly Pro Ala Phe Ser Lys Pro Leu Lys Asp Lys Ile Asn Pro
1               5                   10                  15

Trp Lys Ser Leu Met Val Met Gly Val Tyr Leu Arg Val Gly Met Ala
            20                  25                  30

Glu Ser Pro His Gln Val Phe Asn Val Thr Trp Arg Val Thr Asn Leu
        35                  40                  45

Met Thr Gly Arg Thr Ala Asn Ala Thr Ser Leu Leu Gly Thr Val Gln
    50                  55                  60

Asp Ala Phe Pro Arg Leu Tyr Phe Asp Leu Cys Asp Leu Val Gly Glu
65                  70                  75                  80

Glu Trp Asp Pro Ser Asp Gln Glu Pro Tyr Val Gly Tyr Gly Cys Lys
                85                  90                  95

Tyr Pro Gly Gly Arg Lys Arg Thr Arg Thr Phe Asp Phe Tyr Val Cys
            100                 105                 110

Pro Gly His Thr Val Lys Ser Gly Cys Gly Gly Pro Arg Glu Gly Tyr
            115                 120                 125

Cys Gly Glu Trp Gly Cys Glu Thr Thr Gly Gln Ala Tyr Trp Lys Pro
130                 135                 140

Thr Ser Ser Trp Asp Leu Ile Ser Leu Lys Arg Gly Asn Thr Pro Trp
145                 150                 155                 160

Asp Thr Gly Cys Ser Lys Met Ala Cys Gly Pro Cys Tyr Asp Leu Ser
                165                 170                 175

Lys Val Ser Asn Ser Phe Gln Gly Ala Thr Arg Gly Gly Arg Cys Asn
            180                 185                 190

Pro Leu Val Leu Glu Phe Thr Asp Ala Gly Lys Lys Ala Asn Trp Asp
            195                 200                 205

Gly Pro Lys Ser Trp Gly Leu Arg Leu Tyr Arg Thr Gly Thr Asp Pro
        210                 215                 220

Ile Thr Met Phe Ser Leu Thr Arg Gln Val Leu Asn Ile Gly Pro Arg
225                 230                 235                 240

Ile Pro Ile Gly Pro Asn Pro Val Ile Thr Gly Gln Leu Pro Pro Ser
                245                 250                 255

Arg Pro Val Gln Ile Arg Leu Pro Arg Pro Gln Pro Pro Pro Pro Thr
            260                 265                 270

Gly Ala Ala Ser Ile Val Pro Glu Thr Ala Pro Pro Ser Gln Gln Pro
            275                 280                 285

Gly Thr Gly Asp Arg Leu Leu Asn Leu Val Glu Gly Ala Tyr Gln Ala
        290                 295                 300

Leu Asn Leu Thr Asn Pro Asp Lys Thr Gln Glu Cys Trp Leu Cys
305                 310                 315
```

<210> SEQ ID NO 10
<211> LENGTH: 316
<212> TYPE: PRT
<213> ORGANISM: Artificial Sequence
<220> FEATURE:
<223> OTHER INFORMATION: Derived from Env Xenotropic Murine Leukaemia
      Virus (NZB)
<220> FEATURE:
<221> NAME/KEY: PEPTIDE
<222> LOCATION: (1)..(316)

```
<400> SEQUENCE: 10

Met Leu Val Met Glu Gly Ser Ala Phe Ser Lys Pro Leu Lys Asp Lys
1               5                   10                  15

Ile Asn Pro Trp Gly Pro Leu Ile Val Met Gly Ile Leu Val Arg Ala
            20                  25                  30

Gly Ala Ser Val Gln Arg Asp Ser Pro His Gln Ile Phe Asn Val Thr
        35                  40                  45

Trp Arg Val Thr Asn Leu Met Thr Gly Gln Thr Ala Asn Ala Thr Ser
    50                  55                  60

Leu Leu Gly Thr Met Thr Asp Thr Phe Pro Lys Leu Tyr Phe Asp Leu
65                  70                  75                  80

Cys Asp Leu Val Gly Asp Tyr Trp Asp Asp Pro Glu Pro Asp Ile Gly
                85                  90                  95

Asp Gly Cys Arg Thr Pro Gly Gly Arg Arg Thr Arg Leu Tyr Asp
            100                 105                 110

Phe Tyr Val Cys Pro Gly His Thr Val Pro Ile Gly Cys Gly Gly Pro
            115                 120                 125

Gly Glu Gly Tyr Cys Gly Lys Trp Gly Cys Glu Thr Thr Gly Gln Ala
        130                 135                 140

Tyr Trp Lys Pro Ser Ser Ser Trp Asp Leu Ile Ser Leu Lys Arg Gly
145                 150                 155                 160

Asn Thr Pro Lys Asp Gln Gly Pro Cys Tyr Asp Ser Ser Val Ser Ser
                165                 170                 175

Gly Val Gln Gly Ala Thr Pro Gly Gly Arg Cys Asn Pro Leu Val Leu
            180                 185                 190

Glu Phe Thr Asp Ala Gly Arg Lys Ala Ser Trp Asp Ala Pro Lys Val
        195                 200                 205

Trp Gly Leu Arg Leu Tyr Arg Ser Thr Gly Ala Asp Pro Val Thr Arg
    210                 215                 220

Phe Ser Leu Thr Arg Gln Val Leu Asn Val Gly Pro Arg Val Pro Ile
225                 230                 235                 240

Gly Pro Asn Pro Val Ile Thr Asp Gln Leu Pro Pro Ser Gln Pro Val
                245                 250                 255

Gln Ile Met Leu Pro Arg Pro Pro His Pro Pro Pro Ser Gly Thr Val
            260                 265                 270

Ser Met Val Pro Gly Ala Pro Pro Ser Gln Gln Pro Gly Thr Gly
        275                 280                 285

Asp Arg Leu Leu Asn Leu Val Glu Gly Ala Tyr Gln Ala Leu Asn Leu
    290                 295                 300

Thr Ser Pro Asp Lys Thr Gln Glu Cys Trp Leu Cys
305                 310                 315

<210> SEQ ID NO 11
<211> LENGTH: 313
<212> TYPE: PRT
<213> ORGANISM: Artificial Sequence
<220> FEATURE:
<223> OTHER INFORMATION: Derived from Env Xenotropic Murine Leukaemia
      Virus (Bxv1)
<220> FEATURE:
<221> NAME/KEY: PEPTIDE
<222> LOCATION: (1)..(313)

<400> SEQUENCE: 11

Met Glu Gly Pro Ala Phe Ser Lys Pro Leu Lys Asp Lys Ile Asn Pro
1               5                   10                  15
```

```
Trp Gly Pro Leu Ile Val Ile Gly Ile Leu Val Arg Ala Gly Ala Ser
             20                  25                  30

Val Gln Arg Asp Ser Pro His Gln Val Phe Asn Val Trp Arg Val
         35                  40                  45

Thr Asn Leu Met Thr Gly Gln Thr Ala Asn Ala Thr Ser Leu Leu Gly
 50                  55                  60

Thr Met Thr Asp Thr Phe Pro Lys Leu Tyr Phe Asp Leu Cys Asp Leu
 65                  70                  75                  80

Val Gly Asp His Trp Asp Asp Pro Glu Pro Asp Ile Gly Asp Gly Cys
                 85                  90                  95

Arg Ser Pro Gly Gly Arg Lys Arg Ser Arg Leu Tyr Asp Phe Tyr Val
            100                 105                 110

Cys Pro Gly His Thr Val Pro Ile Gly Cys Gly Gly Pro Gly Glu Gly
            115                 120                 125

Tyr Cys Gly Lys Trp Gly Cys Glu Thr Thr Gly Gln Ala Tyr Trp Lys
            130                 135                 140

Pro Ser Ser Ser Trp Asp Leu Ile Ser Leu Lys Arg Gly Asn Thr Pro
145                 150                 155                 160

Lys Asp Gln Gly Pro Cys Tyr Asp Ser Ser Val Ser Ser Gly Val Gln
                165                 170                 175

Gly Ala Thr Pro Gly Gly Arg Cys Asn Pro Leu Val Leu Glu Phe Thr
            180                 185                 190

Asp Ala Gly Lys Lys Ala Ser Trp Asp Ala Pro Lys Val Trp Gly Leu
            195                 200                 205

Arg Leu Tyr Arg Ser Thr Gly Ala Asp Pro Val Thr Arg Phe Ser Leu
            210                 215                 220

Thr Arg Gln Val Leu Asn Val Gly Pro Arg Val Pro Ile Gly Pro Asn
225                 230                 235                 240

Pro Val Ile Thr Glu Gln Leu Pro Pro Ser Gln Pro Val Gln Ile Met
                245                 250                 255

Leu Pro Arg Pro Pro His Pro Pro Ser Gly Ala Ala Ser Met Val
            260                 265                 270

Pro Gly Ala Pro Pro Pro Ser Gln Gln Pro Gly Thr Gly Asp Arg Leu
            275                 280                 285

Leu Asn Leu Val Lys Gly Ala Tyr Gln Ala Leu Asn Leu Thr Ser Pro
290                 295                 300

Asp Arg Thr Gln Glu Cys Trp Leu Cys
305                 310

<210> SEQ ID NO 12
<211> LENGTH: 314
<212> TYPE: PRT
<213> ORGANISM: Artificial Sequence
<220> FEATURE:
<223> OTHER INFORMATION: Derived from Env XMRV (new Human Murine
      Leukaemia Virus-like)
<220> FEATURE:
<221> NAME/KEY: PEPTIDE
<222> LOCATION: (1)..(314)

<400> SEQUENCE: 12

Met Glu Ser Pro Ala Phe Ser Lys Pro Leu Lys Asp Lys Ile Asn Pro
1               5                   10                  15

Trp Gly Pro Leu Ile Ile Met Gly Ile Leu Val Arg Ala Gly Ala Ser
             20                  25                  30

Val Gln Arg Asp Ser Pro His Gln Val Phe Asn Val Thr Trp Lys Ile
         35                  40                  45
```

```
Thr Asn Leu Met Thr Gly Gln Thr Ala Asn Ala Thr Ser Leu Leu Gly
            50                  55                  60

Thr Met Thr Asp Thr Phe Pro Lys Leu Tyr Phe Asp Leu Cys Asp Leu
 65                  70                  75                  80

Val Gly Asp Asn Trp Asp Asp Pro Glu Pro Asp Ile Gly Asp Gly Cys
                 85                  90                  95

Arg Ser Pro Gly Gly Arg Lys Arg Thr Arg Leu Tyr Asp Phe Tyr Val
                100                 105                 110

Cys Pro Gly His Thr Val Leu Thr Gly Cys Gly Pro Arg Glu Gly
                115                 120                 125

Tyr Cys Gly Lys Trp Gly Cys Glu Thr Thr Gly Gln Ala Tyr Trp Lys
        130                 135                 140

Pro Ser Ser Ser Trp Asp Leu Ile Ser Leu Lys Arg Gly Asn Thr Pro
145                 150                 155                 160

Lys Gly Gln Gly Pro Cys Phe Asp Ser Val Gly Ser Gly Ser Ile
                165                 170                 175

Gln Gly Ala Thr Pro Gly Gly Arg Cys Asn Pro Leu Val Leu Glu Phe
                180                 185                 190

Thr Asp Ala Gly Lys Arg Ala Ser Trp Asp Ala Pro Lys Thr Trp Gly
                195                 200                 205

Leu Arg Leu Tyr Arg Ser Thr Gly Ala Asp Pro Val Thr Leu Phe Ser
        210                 215                 220

Leu Thr Arg Gln Val Leu Asn Val Gly Pro Arg Val Pro Ile Gly Pro
225                 230                 235                 240

Asn Pro Val Ile Thr Glu Gln Leu Pro Ser Gln Pro Val Gln Ile
                245                 250                 255

Met Leu Pro Arg Pro Pro Arg Pro Pro Ser Gly Ala Ala Ser Met
                260                 265                 270

Val Pro Gly Ala Pro Pro Ser Gln Gln Pro Gly Thr Gly Asp Arg
                275                 280                 285

Leu Leu Asn Leu Val Glu Gly Ala Tyr Gln Ala Leu Asn Leu Thr Ser
        290                 295                 300

Pro Asp Lys Thr Gln Glu Cys Trp Leu Cys
305                 310

<210> SEQ ID NO 13
<211> LENGTH: 310
<212> TYPE: PRT
<213> ORGANISM: Artificial Sequence
<220> FEATURE:
<223> OTHER INFORMATION: Derived from Env MCF polytropic Murine
      Leukaemia Virus (MX27)
<220> FEATURE:
<221> NAME/KEY: PEPTIDE
<222> LOCATION: (1)..(310)

<400> SEQUENCE: 13

Met Glu Gly Pro Ala Phe Ser Lys Pro Leu Lys Asp Lys Ile Asn Pro
 1               5                  10                  15

Trp Gly Pro Leu Ile Val Leu Gly Ile Leu Ile Arg Ala Gly Val Ser
                20                  25                  30

Val Gln His Asp Ser Pro His Gln Val Phe Asn Val Thr Trp Arg Val
                35                  40                  45

Thr Asn Leu Met Thr Gly Gln Thr Ala Asn Ala Thr Ser Leu Leu Gly
            50                  55                  60

Thr Met Thr Asp Ala Phe Pro Lys Leu Tyr Phe Asp Leu Cys Asp Leu
```

```
                65                  70                  75                  80
Ile Gly Asp Asp Trp Asp Glu Thr Gly Leu Gly Cys Arg Thr Pro Gly
                    85                  90                  95

Gly Arg Lys Arg Ala Arg Thr Phe Asp Phe Tyr Val Cys Pro Gly His
                100                 105                 110

Thr Val Pro Thr Gly Cys Gly Pro Arg Glu Gly Tyr Cys Gly Lys
                115                 120                 125

Trp Gly Cys Glu Thr Thr Gly Gln Ala Tyr Trp Lys Pro Ser Ser Ser
            130                 135                 140

Trp Asp Leu Ile Ser Leu Lys Arg Gly Asn Thr Pro Arg Asn Gln Gly
145                 150                 155                 160

Pro Cys Tyr Asp Ser Ser Ala Val Ser Ser Asp Ile Lys Gly Ala Thr
                165                 170                 175

Pro Gly Gly Arg Cys Asn Pro Leu Val Leu Glu Phe Thr Asp Ala Gly
                180                 185                 190

Lys Lys Ala Ser Trp Asp Gly Pro Lys Val Trp Gly Leu Arg Leu Tyr
                195                 200                 205

Arg Ser Thr Gly Thr Asp Pro Val Thr Arg Phe Ser Leu Thr Arg Gln
            210                 215                 220

Val Leu Asn Ile Gly Pro Arg Val Pro Ile Gly Pro Asn Pro Val Ile
225                 230                 235                 240

Thr Asp Gln Leu Pro Pro Ser Arg Pro Val Gln Ile Met Leu Pro Arg
                245                 250                 255

Pro Pro Gln Pro Pro Pro Gly Ala Ala Ser Ile Val Pro Glu Thr
                260                 265                 270

Ala Pro Pro Ser Gln Gln Pro Gly Thr Gly Asp Arg Leu Leu Asn Leu
            275                 280                 285

Val Asp Gly Ala Tyr Gln Ala Leu Asn Leu Thr Ser Pro Asp Lys Thr
                290                 295                 300

Gln Glu Cys Trp Leu Cys
305                 310

<210> SEQ ID NO 14
<211> LENGTH: 301
<212> TYPE: PRT
<213> ORGANISM: Artificial Sequence
<220> FEATURE:
<223> OTHER INFORMATION: Derived from Env MCF polytropic Murine
      Leukaemia Virus (MX33)
<220> FEATURE:
<221> NAME/KEY: PEPTIDE
<222> LOCATION: (1)..(301)

<400> SEQUENCE: 14

Met Glu Gly Pro Ala Phe Ser Lys Pro Leu Lys Asp Lys Ile Asn Pro
1               5                   10                  15

Trp Ala Pro Leu Ile Val Leu Gly Ile Leu Ile Arg Ala Gly Val Ser
                20                  25                  30

Val Pro His Asp Ser Pro His Gln Val Phe Asn Val Thr Trp Arg Val
            35                  40                  45

Thr Asn Leu Met Thr Gly Gln Thr Ala Asn Ala Thr Ser Leu Leu Gly
                50                  55                  60

Thr Met Thr Asp Ala Phe Pro Lys Leu Tyr Phe Asp Leu Cys Asp Leu
65                  70                  75                  80

Ile Gly Asp Asp Trp Asp Glu Thr Gly Leu Gly Cys Arg Thr Pro Gly
                    85                  90                  95
```

```
Gly Arg Lys Arg Ala Arg Thr Phe Asp Phe Tyr Val Cys Pro Gly His
                100                 105                 110
Thr Val Pro Thr Gly Cys Gly Pro Arg Glu Gly Tyr Cys Gly Lys
            115                 120                 125
Trp Gly Cys Glu Thr Thr Gly Gln Ala Tyr Trp Lys Pro Ser Ser Ser
130                 135                 140
Trp Asp Leu Ile Ser Leu Lys Arg Gly Asn Thr Pro Arg Asn Gln Gly
145                 150                 155                 160
Pro Cys Tyr Asp Ser Ser Ala Val Ser Ser Gly Ile Gln Gly Ala Thr
                165                 170                 175
Pro Gly Gly Arg Cys Asn Pro Leu Val Leu Glu Phe Thr Asp Ala Gly
            180                 185                 190
Lys Lys Ala Ser Trp Asp Gly Pro Lys Val Trp Gly Leu Arg Leu Tyr
        195                 200                 205
Arg Ser Thr Gly Thr Asp Pro Val Thr Arg Phe Ser Leu Thr Arg Gln
        210                 215                 220
Val Leu Asn Ile Gly Pro Arg Ile Pro Ile Gly Pro Asn Pro Val Ile
225                 230                 235                 240
Thr Asp Gln Leu Pro Pro Ser Arg Pro Val Gln Ile Met Leu Pro Arg
                245                 250                 255
Pro Pro Gln Pro Ser Pro Thr Gly Ala Ala Ser Ile Gln Pro Gly Thr
            260                 265                 270
Gly Asp Arg Leu Leu Asn Leu Val Asp Gly Ala Tyr Gln Ala Leu Asn
        275                 280                 285
Leu Thr Ser Pro Asp Lys Thr Gln Glu Cys Trp Leu Cys
        290                 295                 300

<210> SEQ ID NO 15
<211> LENGTH: 310
<212> TYPE: PRT
<213> ORGANISM: Artificial Sequence
<220> FEATURE:
<223> OTHER INFORMATION: Derived from Env MCF1233 polytropic Murine
      Leukaemia Virus
<220> FEATURE:
<221> NAME/KEY: PEPTIDE
<222> LOCATION: (1)..(310)

<400> SEQUENCE: 15

Met Glu Gly Pro Ala Phe Ser Lys Pro Leu Lys Asp Lys Ile Asn Pro
1               5                   10                  15
Trp Gly Pro Leu Ile Ile Leu Gly Ile Leu Ile Arg Ala Gly Val Ser
            20                  25                  30
Val Gln His Asp Ser Pro His Gln Val Phe Asn Val Thr Trp Arg Val
        35                  40                  45
Thr Asn Leu Met Thr Gly Gln Thr Ala Asn Ala Thr Ser Leu Leu Gly
    50                  55                  60
Thr Met Thr Asp Ala Phe Pro Lys Leu Tyr Phe Asp Leu Cys Asp Leu
65                  70                  75                  80
Ile Gly Asp Asp Trp Asp Glu Thr Gly Leu Gly Cys Arg Thr Pro Gly
                85                  90                  95
Gly Arg Lys Arg Ala Arg Thr Phe Asp Phe Tyr Val Cys Pro Gly His
                100                 105                 110
Thr Val Pro Thr Gly Cys Gly Gly Pro Arg Glu Gly Tyr Cys Gly Lys
            115                 120                 125
Trp Gly Cys Glu Thr Thr Gly Gln Ala Tyr Trp Lys Pro Ser Ser Ser
130                 135                 140
```

```
Trp Asp Leu Ile Ser Leu Lys Arg Gly Asn Thr Pro Gln Asn Gln Gly
145                 150                 155                 160

Pro Cys Tyr Asp Ser Ser Ala Val Ser Asp Ile Lys Gly Ala Thr
            165                 170                 175

Pro Gly Gly Arg Cys Asn Pro Leu Val Leu Glu Phe Thr Asp Ala Gly
            180                 185                 190

Lys Lys Ala Ser Trp Asp Gly Pro Lys Val Trp Gly Leu Arg Leu Tyr
            195                 200                 205

Arg Pro Thr Gly Thr Asp Pro Val Thr Arg Phe Ser Leu Thr Arg Arg
            210                 215                 220

Val Leu Asn Ile Gly Pro Arg Val Pro Ile Gly Pro Asn Pro Val Ile
225                 230                 235                 240

Ala Asp Gln Leu Pro Pro Ser Arg Pro Val Gln Ile Met Leu Pro Arg
            245                 250                 255

Pro Pro Gln Pro Pro Pro Gly Ala Ser Ser Ile Val Pro Glu Thr
            260                 265                 270

Ala Pro Pro Ser Gln Gln Pro Gly Thr Gly Asp Arg Leu Leu Asn Leu
            275                 280                 285

Val Asp Gly Ala Tyr Gln Ala Leu Asn Leu Thr Ser Pro Asp Lys Thr
            290                 295                 300

Gln Glu Cys Trp Leu Cys
305                 310

<210> SEQ ID NO 16
<211> LENGTH: 348
<212> TYPE: PRT
<213> ORGANISM: Artificial Sequence
<220> FEATURE:
<223> OTHER INFORMATION: Derived from Env Mus dunni endogenous virus
<220> FEATURE:
<221> NAME/KEY: PEPTIDE
<222> LOCATION: (1)..(348)

<400> SEQUENCE: 16

Met Lys Lys Pro Thr Lys Thr Thr Gly Leu Trp Lys Pro Leu Ile Thr
1               5                   10                  15

Leu Leu Ser Phe Ala Cys Val Ala Gly Ala Pro Ser Ile Thr Leu Asp
                20                  25                  30

Leu Gly Asn His Asn Pro His Ala Pro Val Gln Gln Ser Trp Glu Val
            35                  40                  45

Leu Asn Glu Lys Gly Asp Val Val Trp Val Ala Thr Ala Val His Pro
50                  55                  60

Pro Trp Thr Trp Trp Pro Asp Leu Thr Pro Asp Ile Cys Lys Leu Ala
65                  70                  75                  80

Ala Gly Ser Pro Asn Trp Asp Leu Pro Asp His Thr Asp Leu Asn Asn
                85                  90                  95

Pro Pro Ser Glu Gln Lys Cys Val Pro Asn Gly Val Gly Ser Thr Thr
            100                 105                 110

Gly Cys Ser Gly Gln Phe Tyr Arg Ala Asn Leu Arg Ala Ala Gln Phe
            115                 120                 125

Tyr Val Cys Pro Gly Gln Gly Gln Lys Gly Lys Leu Gln Gln Glu Cys
            130                 135                 140

Arg Gly Ala Ser Asp Tyr Phe Cys Gly Lys Trp Thr Cys Glu Thr Thr
145                 150                 155                 160

Gly Glu Ala Tyr Trp Lys Pro Ser Ala Asp Trp Asp Leu Ile Thr Val
            165                 170                 175
```

```
Lys Arg Gly Ser Gly Tyr Asp Lys Pro Asn Gln Gly Glu Arg Asn Pro
            180                 185                 190

Tyr Lys Tyr Leu Asp Ser Gly Cys Ala Leu Lys Asn Tyr Ser Pro Pro
        195                 200                 205

Gly Pro Cys Lys Gly Lys Tyr Cys Asn Pro Leu Leu Ile Lys Phe Thr
    210                 215                 220

Glu Lys Gly Lys Gln Ala Arg Leu Ser Trp Leu Lys Gly Asn Arg Trp
225                 230                 235                 240

Gly Trp Arg Val Tyr Ile Pro Ile Arg Asp Pro Gly Phe Ile Phe Thr
                245                 250                 255

Ile Arg Leu Thr Val Arg Asp Leu Ala Val Thr Ser Ile Gly Pro Asn
                260                 265                 270

Lys Val Leu Thr Glu Gln Ala Pro Pro Val Ala Pro Ala Pro Pro Arg
            275                 280                 285

Val Pro Ala Val Pro Ala Pro Pro Thr Ser Arg Pro Tyr Thr Val Gly
        290                 295                 300

Pro Ser Leu Glu Thr Thr Leu Ala Ser Pro Pro Leu Leu Asp Thr Glu
305                 310                 315                 320

Asn Arg Leu Val Ser Leu Val Gln Gly Ala Phe Leu Val Leu Asn Arg
                325                 330                 335

Thr Asn Pro Asn Met Thr Gln Ser Cys Trp Leu Cys
            340                 345

<210> SEQ ID NO 17
<211> LENGTH: 315
<212> TYPE: PRT
<213> ORGANISM: Artificial Sequence
<220> FEATURE:
<223> OTHER INFORMATION: Derived from Env Feline Leukaemia Virus A
<220> FEATURE:
<221> NAME/KEY: PEPTIDE
<222> LOCATION: (1)..(315)

<400> SEQUENCE: 17

Met Glu Ser Pro Thr His Pro Lys Pro Ser Lys Asp Lys Thr Leu Ser
1               5                   10                  15

Trp Asn Leu Ala Phe Leu Val Gly Ile Leu Phe Thr Ile Asp Ile Gly
            20                  25                  30

Met Ala Asn Pro Ser Pro His Gln Ile Tyr Asn Val Thr Trp Val Ile
        35                  40                  45

Thr Asn Val Gln Thr Asn Thr Gln Ala Asn Ala Thr Ser Met Leu Gly
    50                  55                  60

Thr Leu Thr Asp Ala Tyr Pro Thr Leu His Val Asp Leu Cys Asp Leu
65                  70                  75                  80

Val Gly Asp Thr Trp Glu Pro Ile Val Leu Asn Pro Thr Asn Val Lys
                85                  90                  95

His Gly Ala Arg Tyr Ser Ser Ser Lys Tyr Gly Cys Lys Thr Thr Asp
            100                 105                 110

Arg Lys Lys Gln Gln Gln Thr Tyr Pro Phe Tyr Val Cys Pro Gly His
        115                 120                 125

Ala Pro Ser Leu Gly Pro Lys Gly Thr His Cys Gly Gly Ala Gln Asp
    130                 135                 140

Gly Phe Cys Ala Ala Trp Gly Cys Glu Thr Thr Gly Glu Ala Trp Trp
145                 150                 155                 160

Lys Pro Thr Ser Ser Trp Asp Tyr Ile Thr Val Lys Arg Gly Ser Ser
                165                 170                 175
```

```
Gln Asp Asn Ser Cys Glu Gly Lys Cys Asn Pro Leu Val Leu Gln Phe
            180                 185                 190

Thr Gln Lys Gly Arg Gln Ala Ser Trp Asp Gly Pro Lys Met Trp Gly
        195                 200                 205

Leu Arg Leu Tyr Arg Thr Gly Tyr Asp Pro Ile Ala Leu Phe Thr Val
    210                 215                 220

Ser Arg Gln Val Ser Thr Ile Thr Pro Pro Gln Ala Met Gly Pro Asn
225                 230                 235                 240

Leu Val Leu Pro Asp Gln Lys Pro Pro Ser Arg Gln Ser Gln Thr Gly
                245                 250                 255

Ser Lys Val Ala Thr Gln Arg Pro Gln Thr Asn Glu Ser Ala Pro Arg
            260                 265                 270

Ser Val Ala Pro Thr Thr Met Gly Pro Lys Arg Ile Gly Thr Gly Asp
        275                 280                 285

Arg Leu Ile Asn Leu Val Gln Gly Thr Tyr Leu Ala Leu Asn Ala Thr
    290                 295                 300

Asp Pro Asn Lys Thr Lys Asp Cys Trp Leu Cys
305                 310                 315

<210> SEQ ID NO 18
<211> LENGTH: 335
<212> TYPE: PRT
<213> ORGANISM: Artificial Sequence
<220> FEATURE:
<223> OTHER INFORMATION: Derived from Env Feline Leukaemia Virus B
<220> FEATURE:
<221> NAME/KEY: PEPTIDE
<222> LOCATION: (1)..(335)

<400> SEQUENCE: 18

Met Glu Ser Pro Thr His Pro Lys Pro Ser Lys Asp Lys Thr Leu Ser
1               5                   10                  15

Trp Asn Leu Val Phe Leu Val Gly Ile Leu Phe Thr Ile Asp Ile Gly
            20                  25                  30

Met Ala Asn Pro Ser Pro His Gln Val Tyr Asn Val Thr Trp Thr Ile
        35                  40                  45

Thr Asn Leu Val Thr Gly Thr Lys Ala Asn Ala Thr Ser Met Leu Gly
    50                  55                  60

Thr Leu Thr Asp Ala Phe Pro Thr Met Tyr Phe Asp Leu Cys Asp Ile
65                  70                  75                  80

Ile Gly Asn Thr Trp Asn Pro Ser Asp Gln Glu Pro Phe Pro Gly Tyr
                85                  90                  95

Gly Cys Asp Gln Pro Met Arg Arg Trp Gln Gln Arg Asn Thr Pro Phe
            100                 105                 110

Tyr Val Cys Pro Gly His Ala Asn Arg Lys Gln Cys Gly Gly Pro Gln
        115                 120                 125

Asp Gly Phe Cys Ala Val Trp Gly Cys Glu Thr Thr Gly Glu Thr Tyr
    130                 135                 140

Trp Arg Pro Thr Ser Ser Trp Asp Tyr Ile Thr Val Lys Lys Gly Val
145                 150                 155                 160

Thr Gln Gly Ile Tyr Gln Cys Ser Gly Gly Trp Cys Gly Pro Cys
                165                 170                 175

Tyr Asp Lys Ala Val His Ser Ser Thr Thr Gly Ala Ser Glu Gly Gly
            180                 185                 190

Arg Cys Asn Pro Leu Ile Leu Gln Phe Thr Gln Lys Gly Arg Gln Thr
        195                 200                 205
```

```
Ser Trp Asp Gly Pro Lys Ser Trp Gly Leu Arg Leu Tyr Arg Ser Gly
    210                 215                 220

Tyr Asp Pro Ile Ala Leu Phe Ser Val Ser Arg Gln Val Met Thr Ile
225                 230                 235                 240

Thr Pro Pro Gln Ala Met Gly Pro Asn Leu Val Leu Pro Asp Gln Lys
                245                 250                 255

Pro Pro Ser Arg Gln Ser Gln Ile Glu Ser Arg Val Thr Pro His His
                260                 265                 270

Ser Gln Gly Asn Gly Gly Thr Pro Gly Ile Thr Leu Val Asn Ala Ser
                275                 280                 285

Ile Ala Pro Leu Ser Thr Pro Val Thr Pro Ala Ser Pro Lys Arg Ile
    290                 295                 300

Gly Thr Gly Asp Arg Leu Ile Asn Leu Val Gln Gly Thr Tyr Leu Ala
305                 310                 315                 320

Leu Asn Ala Thr Asp Pro Asn Arg Thr Lys Asp Cys Trp Leu Cys
                325                 330                 335

<210> SEQ ID NO 19
<211> LENGTH: 312
<212> TYPE: PRT
<213> ORGANISM: Artificial Sequence
<220> FEATURE:
<223> OTHER INFORMATION: Derived from Env Feline Leukaemia Virus C
<220> FEATURE:
<221> NAME/KEY: PEPTIDE
<222> LOCATION: (1)..(312)

<400> SEQUENCE: 19

Met Glu Ser Pro Thr His Pro Lys Pro Ser Lys Asp Lys Thr Phe Pro
1               5                   10                  15

Trp Asn Leu Val Phe Leu Val Gly Ile Leu Phe Gln Ile Asp Met Gly
                20                  25                  30

Met Ala Asn Pro Ser Pro His Gln Val Tyr Asn Val Thr Trp Val Ile
            35                  40                  45

Thr Asn Val Gln Thr Asn Ser Arg Ala Asn Ala Thr Ser Met Leu Gly
50                  55                  60

Thr Leu Thr Asp Ala Tyr Pro Thr Leu Tyr Val Asp Leu Cys Asp Leu
65                  70                  75                  80

Val Gly Asp Thr Trp Glu Pro Ile Ala Pro Asp Pro Arg Ser Trp Ala
                85                  90                  95

Arg Tyr Ser Ser Ser Thr His Gly Cys Lys Thr Thr Asp Arg Lys Lys
            100                 105                 110

Gln Gln Gln Thr Tyr Pro Phe Tyr Val Cys Pro Gly His Ala Pro Ser
        115                 120                 125

Met Gly Pro Lys Gly Thr Tyr Cys Gly Gly Ala Gln Asp Gly Phe Cys
    130                 135                 140

Ala Ala Trp Gly Cys Glu Thr Thr Gly Glu Ala Trp Trp Lys Pro Thr
145                 150                 155                 160

Ser Ser Trp Asp Tyr Ile Thr Val Lys Arg Gly Ser Asn Gln Asp Asn
                165                 170                 175

Ser Cys Lys Gly Lys Cys Asn Pro Leu Val Leu Gln Phe Thr Gln Lys
            180                 185                 190

Gly Arg Gln Ala Ser Trp Asp Arg Pro Lys Met Trp Gly Leu Arg Leu
        195                 200                 205

Tyr Arg Ser Gly Tyr Asp Pro Ile Ala Leu Phe Ser Val Ser Arg Gln
    210                 215                 220
```

```
Val Met Thr Ile Thr Pro Pro Gln Ala Met Gly Pro Asn Leu Val Leu
225                 230                 235                 240

Pro Asp Gln Lys Pro Pro Ser Arg Gln Ser Gln Thr Lys Ser Lys Val
                245                 250                 255

Thr Thr Gln Arg Pro Gln Ile Thr Ser Ser Thr Pro Arg Ser Val Ala
            260                 265                 270

Ser Ala Thr Met Gly Pro Lys Arg Ile Gly Thr Gly Asp Arg Leu Ile
        275                 280                 285

Asn Leu Val Gln Gly Thr Tyr Leu Ala Leu Asn Ala Thr Asp Pro Asn
    290                 295                 300

Lys Thr Lys Asp Cys Trp Leu Cys
305                 310

<210> SEQ ID NO 20
<211> LENGTH: 331
<212> TYPE: PRT
<213> ORGANISM: Artificial Sequence
<220> FEATURE:
<223> OTHER INFORMATION: Derived from Env Koala Retrovirus
<220> FEATURE:
<221> NAME/KEY: PEPTIDE
<222> LOCATION: (1)..(331)

<400> SEQUENCE: 20

Met Leu Leu Ile Ser Asn Pro Arg His Leu Gly His Pro Met Ser Pro
1               5                   10                  15

Gly Asn Trp Lys Arg Leu Ile Ile Leu Leu Ser Cys Val Phe Gly Gly
            20                  25                  30

Ala Glu Met Asn Gln Gln His Asn Asn Pro His Gln Pro Met Thr Leu
        35                  40                  45

Thr Trp Gln Val Leu Ser Gln Thr Gly Ser Val Val Trp Glu Lys Lys
    50                  55                  60

Ala Val Glu Pro Pro Trp Thr Trp Trp Pro Ser Leu Glu Pro Asp Val
65                  70                  75                  80

Cys Ala Leu Val Ala Gly Leu Glu Ser Trp Asp Ile Pro Glu Leu Thr
                85                  90                  95

Ala Ser Ala Ser Gln Gln Ala Arg Pro Pro Asp Ser Asn Tyr Glu His
            100                 105                 110

Ala Tyr Asn Gln Ile Thr Trp Gly Thr Leu Gly Cys Ser Tyr Pro Arg
        115                 120                 125

Ala Arg Thr Arg Ile Ala Arg Ser Gln Phe Tyr Val Cys Pro Arg Asp
    130                 135                 140

Gly Arg Ser Leu Ser Glu Ala Arg Arg Cys Gly Gly Leu Glu Ser Leu
145                 150                 155                 160

Tyr Cys Lys Glu Trp Gly Cys Glu Thr Ala Gly Thr Ala Tyr Trp Gln
                165                 170                 175

Pro Arg Ser Ser Trp Asp Leu Ile Thr Val Gly Gln Gly His Pro Thr
            180                 185                 190

Gly Thr Cys Glu Arg Thr Gly Trp Cys Asn Pro Leu Lys Ile Glu Phe
        195                 200                 205

Thr Glu Pro Gly Lys Arg Phe Arg Asn Trp Leu Gln Gly Arg Thr Trp
    210                 215                 220

Gly Leu Arg Phe Tyr Val Thr Gly His Pro Gly Val Gln Leu Thr Ile
225                 230                 235                 240

Arg Leu Val Ile Thr Ser Pro Pro Val Val Gly Pro Asp Pro
                245                 250                 255
```

```
Val Leu Ala Glu Gln Gly Pro Pro Arg Lys Ile Pro Phe Leu Pro Arg
                260                 265                 270

Val Pro Val Pro Thr Leu Ser Pro Ala Ser Pro Ile Pro Thr Val
            275                 280                 285

Gln Ala Ser Pro Ala Pro Ser Thr Pro Ser Pro Thr Thr Gly Asp
        290                 295                 300

Arg Leu Phe Gly Leu Val Gln Gly Ala Phe Leu Ala Leu Asn Ala Thr
305                 310                 315                 320

Asn Pro Glu Ala Thr Glu Ser Cys Trp Leu Cys
                325                 330

<210> SEQ ID NO 21
<211> LENGTH: 329
<212> TYPE: PRT
<213> ORGANISM: Artificial Sequence
<220> FEATURE:
<223> OTHER INFORMATION: Derived from Env Porcine Endogenous
      Retrovirus-A
<220> FEATURE:
<221> NAME/KEY: PEPTIDE
<222> LOCATION: (1)..(329)

<400> SEQUENCE: 21

Met His Pro Thr Leu Ser Arg Arg His Leu Pro Ile Arg Gly Gly Lys
1               5                   10                  15

Pro Lys Arg Leu Lys Ile Pro Leu Ser Phe Ala Ser Ile Ala Trp Phe
                20                  25                  30

Leu Thr Leu Ser Ile Thr Pro Gln Val Asn Gly Lys Arg Leu Val Asp
            35                  40                  45

Ser Pro Asn Ser His Lys Pro Leu Ser Leu Thr Trp Leu Leu Thr Asp
50                  55                  60

Ser Gly Thr Gly Ile Asn Ile Asn Ser Thr Gln Gly Glu Ala Pro Leu
65                  70                  75                  80

Gly Thr Trp Trp Pro Glu Leu Tyr Val Cys Leu Arg Ser Val Ile Pro
                85                  90                  95

Gly Leu Asn Asp Gln Ala Thr Pro Pro Asp Val Leu Arg Ala Tyr Gly
                100                 105                 110

Phe Tyr Val Cys Pro Gly Pro Pro Asn Asn Glu Glu Tyr Cys Gly Asn
            115                 120                 125

Pro Gln Asp Phe Phe Cys Lys Gln Trp Ser Cys Ile Thr Ser Asn Asp
        130                 135                 140

Gly Asn Trp Lys Trp Pro Val Ser Gln Gln Asp Arg Val Ser Tyr Ser
145                 150                 155                 160

Phe Val Asn Asn Pro Thr Ser Tyr Asn Gln Phe Asn Tyr Gly His Gly
                165                 170                 175

Arg Trp Lys Asp Trp Gln Gln Arg Val Gln Lys Asp Val Arg Asn Lys
            180                 185                 190

Gln Ile Ser Cys His Ser Leu Asp Leu Asp Tyr Leu Lys Ile Ser Phe
        195                 200                 205

Thr Glu Lys Gly Lys Gln Glu Asn Ile Gln Lys Trp Val Asn Gly Ile
    210                 215                 220

Ser Trp Gly Ile Val Tyr Tyr Gly Gly Ser Gly Arg Lys Lys Gly Ser
225                 230                 235                 240

Val Leu Thr Ile Arg Leu Arg Ile Glu Thr Gln Met Glu Pro Pro Val
                245                 250                 255

Ala Ile Gly Pro Asn Lys Gly Leu Ala Glu Gln Gly Pro Pro Ile Gln
```

```
            260                 265                 270
Glu Gln Arg Pro Ser Pro Asn Pro Ser Asp Tyr Asn Thr Thr Ser Gly
            275                 280                 285
Ser Val Pro Thr Glu Pro Asn Ile Thr Ile Lys Thr Gly Ala Lys Leu
        290                 295                 300
Phe Ser Leu Ile Gln Gly Ala Phe Gln Ala Leu Asn Ser Thr Thr Pro
305                 310                 315                 320
Glu Ala Thr Ser Ser Cys Trp Leu Cys
            325

<210> SEQ ID NO 22
<211> LENGTH: 326
<212> TYPE: PRT
<213> ORGANISM: Artificial Sequence
<220> FEATURE:
<223> OTHER INFORMATION: Derived from Env Porcine Endogeneous
      Retrovirus-B
<220> FEATURE:
<221> NAME/KEY: PEPTIDE
<222> LOCATION: (1)..(326)

<400> SEQUENCE: 22

Met His Pro Thr Leu Ser Trp Arg His Leu Pro Thr Arg Gly Gly Glu
1               5                   10                  15
Pro Lys Arg Leu Arg Ile Pro Leu Ser Phe Ala Ser Ile Ala Trp Phe
            20                  25                  30
Leu Thr Leu Thr Ile Thr Pro Gln Ala Ser Ser Lys Arg Leu Ile Asp
        35                  40                  45
Ser Ser Asn Pro His Arg Pro Leu Ser Leu Thr Trp Leu Ile Ile Asp
    50                  55                  60
Pro Asp Thr Gly Val Thr Val Asn Ser Thr Arg Gly Val Ala Pro Arg
65                  70                  75                  80
Gly Thr Trp Trp Pro Glu Leu His Phe Cys Leu Arg Leu Ile Asn Pro
                85                  90                  95
Ala Val Lys Ser Thr Pro Pro Asn Leu Val Arg Ser Tyr Gly Phe Tyr
            100                 105                 110
Cys Cys Pro Gly Thr Glu Lys Glu Lys Tyr Cys Gly Gly Ser Gly Glu
        115                 120                 125
Ser Phe Cys Arg Arg Trp Ser Cys Val Thr Ser Asn Asp Gly Asp Trp
    130                 135                 140
Lys Trp Pro Ile Ser Leu Gln Asp Arg Val Lys Phe Ser Phe Val Asn
145                 150                 155                 160
Ser Gly Pro Gly Lys Tyr Lys Val Met Lys Leu Tyr Lys Asp Lys Ser
                165                 170                 175
Cys Ser Pro Ser Asp Leu Asp Tyr Leu Lys Ile Ser Phe Thr Glu Lys
            180                 185                 190
Gly Lys Gln Glu Asn Ile Gln Lys Trp Ile Asn Gly Met Ser Trp Gly
        195                 200                 205
Ile Val Phe Tyr Lys Tyr Gly Gly Ala Gly Ser Thr Leu Thr Ile
    210                 215                 220
Arg Leu Arg Ile Glu Thr Gly Thr Glu Pro Val Ala Val Gly Pro
225                 230                 235                 240
Asp Lys Val Leu Ala Glu Gln Gly Pro Pro Ala Leu Glu Pro Pro His
                245                 250                 255
Asn Leu Pro Val Pro Gln Leu Thr Ser Leu Arg Pro Asp Ile Thr Gln
            260                 265                 270
```

```
Pro Pro Ser Asn Gly Thr Thr Gly Leu Ile Pro Thr Asn Thr Pro Arg
            275                 280                 285

Asn Ser Pro Gly Val Pro Val Lys Thr Gly Gln Arg Leu Phe Ser Leu
        290                 295                 300

Ile Gln Gly Ala Phe Gln Ala Ile Asn Ser Thr Asp Pro Asp Ala Thr
305                 310                 315                 320

Ser Ser Cys Trp Leu Cys
                325

<210> SEQ ID NO 23
<211> LENGTH: 305
<212> TYPE: PRT
<213> ORGANISM: Artificial Sequence
<220> FEATURE:
<223> OTHER INFORMATION: Derived from Env Human Endogeneous Retrovirus-T
<220> FEATURE:
<221> NAME/KEY: PEPTIDE
<222> LOCATION: (1)..(305)

<400> SEQUENCE: 23

Met Gly Pro Glu Ala Trp Val Arg Pro Leu Lys Thr Ala Pro Lys Pro
1               5                   10                  15

Gly Glu Ala Ile Arg Leu Ile Leu Phe Ile Tyr Leu Ser Cys Phe Phe
            20                  25                  30

Leu Pro Val Met Ser Ser Glu Pro Ser Tyr Ser Phe Leu Leu Thr Ser
        35                  40                  45

Phe Thr Thr Gly Arg Val Phe Ala Asn Thr Thr Trp Arg Ala Gly Thr
50                  55                  60

Ser Lys Glu Val Ser Phe Ala Val Asp Leu Cys Val Leu Phe Pro Glu
65                  70                  75                  80

Pro Ala Arg Thr His Glu Glu Gln His Asn Leu Pro Val Ile Gly Ala
                85                  90                  95

Gly Ser Val Asp Leu Ala Ala Gly Phe Gly His Ser Gly Ser Gln Thr
            100                 105                 110

Gly Cys Gly Ser Ser Lys Gly Ala Glu Lys Gly Leu Gln Asn Val Asp
        115                 120                 125

Phe Tyr Leu Cys Pro Gly Asn His Pro Asp Ala Ser Cys Arg Asp Thr
130                 135                 140

Tyr Gln Phe Phe Cys Pro Asp Trp Thr Cys Val Thr Leu Ala Thr Tyr
145                 150                 155                 160

Ser Gly Gly Ser Thr Arg Ser Ser Thr Leu Ser Ile Ser Arg Val Pro
                165                 170                 175

His Pro Lys Leu Cys Thr Arg Lys Asn Cys Asn Pro Leu Thr Ile Thr
            180                 185                 190

Val His Asp Pro Asn Ala Ala Gln Trp Tyr Tyr Gly Met Ser Trp Gly
        195                 200                 205

Leu Arg Leu Tyr Ile Pro Gly Phe Asp Val Gly Thr Met Phe Thr Ile
210                 215                 220

Gln Lys Lys Ile Leu Val Ser Trp Ser Ser Pro Lys Pro Ile Gly Pro
225                 230                 235                 240

Leu Thr Asp Leu Gly Asp Pro Ile Phe Gln Lys His Pro Asp Lys Val
                245                 250                 255

Asp Leu Thr Val Pro Leu Pro Phe Leu Val Pro Arg Pro Gln Leu Gln
            260                 265                 270

Gln Gln His Leu Gln Pro Ser Leu Met Ser Ile Leu Gly Gly Val His
        275                 280                 285
```

His Leu Asn Leu Thr Gln Pro Lys Leu Ala Gln Asp Cys Trp Leu
            290                 295                 300

Cys
305

<210> SEQ ID NO 24
<211> LENGTH: 189
<212> TYPE: PRT
<213> ORGANISM: Artificial Sequence
<220> FEATURE:
<223> OTHER INFORMATION: Derived from Env Human Endogeneous Retrovirus-W
<220> FEATURE:
<221> NAME/KEY: PEPTIDE
<222> LOCATION: (1)..(189)

<400> SEQUENCE: 24

Met Ala Leu Pro Tyr His Ile Phe Leu Phe Thr Val Val Ser Pro Ser
1               5                   10                  15

Phe Thr Leu Thr Ala Pro Pro Cys Arg Cys Met Thr Ser Ser Ser
            20                  25                  30

Pro Tyr Gln Glu Phe Leu Trp Arg Met Gln Arg Pro Gly Asn Ile Asp
            35                  40                  45

Ala Pro Ser Tyr Arg Ser Leu Cys Lys Gly Thr Pro Thr Phe Thr Ala
    50                  55                  60

His Thr His Met Pro Arg Asn Cys Tyr His Ser Ala Thr Leu Cys Met
65                  70                  75                  80

His Ala Asn Thr His Tyr Trp Thr Gly Lys Met Ile Asn Pro Ser Cys
                85                  90                  95

Pro Gly Gly Leu Gly Val Thr Val Cys Trp Thr Tyr Phe Thr Gln Thr
            100                 105                 110

Gly Met Ser Asp Gly Gly Val Gln Asp Gln Ala Arg Glu Lys His
            115                 120                 125

Val Lys Glu Val Ile Ser Gln Leu Thr Arg Val His Gly Thr Ser Ser
130                 135                 140

Pro Tyr Lys Gly Leu Asp Leu Ser Lys Leu His Glu Thr Leu Arg Thr
145                 150                 155                 160

His Thr Arg Leu Val Ser Leu Phe Asn Thr Thr Leu Thr Gly Leu His
                165                 170                 175

Glu Val Ser Ala Gln Asn Pro Thr Asn Cys Trp Ile Cys
            180                 185

<210> SEQ ID NO 25
<211> LENGTH: 295
<212> TYPE: PRT
<213> ORGANISM: Artificial Sequence
<220> FEATURE:
<223> OTHER INFORMATION: Derived from Env Human Endogeneous Retrovirus-R
<220> FEATURE:
<221> NAME/KEY: PEPTIDE
<222> LOCATION: (1)..(295)

<400> SEQUENCE: 25

Met Leu Gly Met Asn Met Leu Ile Thr Leu Phe Leu Leu Leu Pro
1               5                   10                  15

Leu Ser Met Leu Lys Gly Glu Pro Trp Glu Cys Leu His Cys Thr
            20                  25                  30

His Thr Thr Trp Ser Gly Asn Ile Met Thr Lys Thr Leu Leu Tyr His
            35                  40                  45

Thr Tyr Tyr Glu Cys Ala Gly Thr Cys Leu Gly Thr Cys Thr His Asn
    50                  55                  60

```
Gln Thr Thr Tyr Ser Val Cys Asp Pro Gly Arg Gly Gln Pro Tyr Val
 65                  70                  75                  80

Cys Tyr Asp Pro Lys Ser Ser Pro Gly Thr Trp Phe Glu Ile His Val
                 85                  90                  95

Gly Ser Lys Glu Gly Asp Leu Leu Asn Gln Thr Lys Val Phe Pro Ser
            100                 105                 110

Gly Lys Asp Val Val Ser Leu Tyr Phe Asp Val Cys Gln Ile Val Ser
        115                 120                 125

Met Gly Ser Leu Phe Pro Val Ile Phe Ser Ser Met Glu Tyr Tyr Ser
    130                 135                 140

Ser Cys His Lys Asn Arg Tyr Ala His Pro Ala Cys Ser Thr Asp Ser
145                 150                 155                 160

Pro Val Thr Thr Cys Trp Asp Cys Thr Thr Trp Ser Thr Asn Gln Gln
                165                 170                 175

Ser Leu Gly Pro Ile Met Leu Thr Lys Ile Pro Leu Glu Pro Asp Cys
            180                 185                 190

Lys Thr Ser Thr Cys Asn Ser Val Asn Leu Thr Ile Leu Glu Pro Asp
        195                 200                 205

Gln Pro Ile Trp Thr Thr Gly Leu Lys Ala Pro Leu Gly Ala Arg Val
    210                 215                 220

Ser Gly Glu Glu Ile Gly Pro Gly Ala Tyr Val Tyr Leu Tyr Ile Ile
225                 230                 235                 240

Lys Lys Thr Arg Thr Arg Ser Thr Gln Gln Phe Arg Val Phe Glu Ser
                245                 250                 255

Phe Tyr Glu His Val Asn Gln Lys Leu Pro Glu Pro Pro Leu Ala
            260                 265                 270

Ser Asn Leu Phe Ala Gln Leu Ala Glu Asn Ile Ala Ser Ser Leu His
        275                 280                 285

Val Ala Ser Cys Tyr Val Cys
    290                 295

<210> SEQ ID NO 26
<211> LENGTH: 283
<212> TYPE: PRT
<213> ORGANISM: Artificial Sequence
<220> FEATURE:
<223> OTHER INFORMATION: Derived from Env Human Endogenous Retrovirus-F
<220> FEATURE:
<221> NAME/KEY: PEPTIDE
<222> LOCATION: (1)..(283)

<400> SEQUENCE: 26

Met Asn Ser Pro Cys Asp Arg Leu Gln Gln Phe Ile Gln Val Leu Leu
1               5                   10                  15

Glu Glu Ser Trp Ser Phe Pro Ser Phe Ala Asn Thr Leu His Trp Pro
            20                  25                  30

Glu Asn Leu Leu Ser Tyr Ile Asp Glu Leu Val Trp Gln Gly Ser Leu
        35                  40                  45

Gln Asn Phe His Gln His Glu Val Arg Phe Asp Lys Pro Pro Leu Arg
    50                  55                  60

Leu Pro Leu Thr Gly Phe Ser Ser Leu Thr Glu Asn Trp Ser Ser Arg
65                  70                  75                  80

Gln Ala Val Ser Ser Arg Leu Val Ala Thr Ala Ser Pro Pro Ala
            85                  90                  95

Gly Cys Gln Ala Pro Ile Ala Phe Leu Gly Leu Lys Phe Ser Ser Leu
            100                 105                 110
```

```
Gly Pro Ala Arg Lys Asn Pro Ala Leu Cys Phe Leu Tyr Asp Gln Ser
            115                 120                 125

Asn Ser Lys Cys Asn Thr Ser Trp Val Lys Glu Asn Val Gly Cys Pro
        130                 135                 140

Trp His Trp Cys Asn Ile His Glu Ala Leu Ile Arg Thr Glu Lys Gly
145                 150                 155                 160

Ser Asp Pro Met Phe Tyr Val Asn Thr Ser Thr Gly Arg Asp Gly
                165                 170                 175

Phe Asn Gly Phe Asn Leu Gln Ile Ser Asp Pro Trp Asp Pro Arg Trp
            180                 185                 190

Ala Ser Gly Val Asp Gly Gly Leu Tyr Glu His Lys Thr Phe Met Tyr
            195                 200                 205

Pro Val Ala Lys Ile Arg Ile Ala Arg Thr Leu Lys Thr Thr Val Thr
            210                 215                 220

Gly Leu Ser Asp Leu Ala Ser Ser Ile Gln Ser Ala Glu Lys Glu Leu
225                 230                 235                 240

Thr Ser Gln Leu Gln Pro Ala Ala Asp Gln Ala Lys Ser Ser Arg Phe
                245                 250                 255

Ser Trp Leu Thr Leu Ile Ser Glu Gly Ala Gln Leu Leu Gln Ser Thr
            260                 265                 270

Gly Val Gln Asn Leu Ser His Cys Phe Leu Cys
            275                 280

<210> SEQ ID NO 27
<211> LENGTH: 228
<212> TYPE: PRT
<213> ORGANISM: Artificial Sequence
<220> FEATURE:
<223> OTHER INFORMATION: Derived from Env Human T Leukaemia Virus-1
<220> FEATURE:
<221> NAME/KEY: PEPTIDE
<222> LOCATION: (1)..(228)

<400> SEQUENCE: 27

Met Gly Lys Phe Leu Ala Thr Leu Ile Leu Phe Phe Gln Phe Cys Pro
1               5                   10                  15

Leu Ile Phe Gly Asp Tyr Ser Pro Ser Cys Cys Thr Leu Thr Ile Gly
                20                  25                  30

Val Ser Ser Tyr His Ser Lys Pro Cys Asn Pro Ala Gln Pro Val Cys
            35                  40                  45

Ser Trp Thr Leu Asp Leu Leu Ala Leu Ser Ala Asp Gln Ala Leu Gln
50                  55                  60

Pro Pro Cys Pro Asn Leu Val Ser Tyr Ser Ser Tyr His Ala Thr Tyr
65                  70                  75                  80

Ser Leu Tyr Leu Phe Pro His Trp Thr Lys Lys Pro Asn Arg Asn Gly
                85                  90                  95

Gly Gly Tyr Tyr Ser Ala Ser Tyr Ser Asp Pro Cys Ser Leu Lys Cys
            100                 105                 110

Pro Tyr Leu Gly Cys Gln Ser Trp Thr Cys Pro Tyr Thr Gly Ala Val
            115                 120                 125

Ser Ser Pro Tyr Trp Lys Phe Gln His Asp Val Asn Phe Thr Gln Glu
            130                 135                 140

Val Ser Arg Leu Asn Ile Asn Leu His Phe Ser Lys Cys Gly Phe Pro
145                 150                 155                 160

Phe Ser Leu Leu Val Asp Ala Pro Gly Tyr Asp Pro Ile Trp Phe Leu
                165                 170                 175
```

```
Asn Thr Glu Pro Ser Gln Leu Pro Pro Thr Ala Pro Pro Leu Leu Pro
            180                 185                 190

His Ser Asn Leu Asp His Ile Leu Glu Pro Ser Ile Pro Trp Lys Ser
            195                 200                 205

Lys Leu Leu Thr Leu Val Gln Leu Thr Leu Gln Ser Thr Asn Tyr Thr
210                 215                 220

Cys Ile Val Cys
225

<210> SEQ ID NO 28
<211> LENGTH: 224
<212> TYPE: PRT
<213> ORGANISM: Artificial Sequence
<220> FEATURE:
<223> OTHER INFORMATION: Derived from Env Human T Leukaemia Virus-2
<220> FEATURE:
<221> NAME/KEY: PEPTIDE
<222> LOCATION: (1)..(224)

<400> SEQUENCE: 28

Met Gly Asn Val Phe Phe Leu Leu Phe Ser Leu Thr His Phe Pro
1               5                   10                  15

Leu Ala Gln Gln Ser Arg Cys Thr Leu Thr Val Gly Ile Ser Ser Tyr
            20                  25                  30

His Ser Ser Pro Cys Ser Pro Thr Gln Pro Val Cys Thr Trp Asn Leu
        35                  40                  45

Asp Leu Asn Ser Leu Thr Thr Asp Gln Arg Leu His Pro Pro Cys Pro
    50                  55                  60

Asn Leu Ile Thr Tyr Ser Gly Phe His Lys Thr Tyr Ser Leu Tyr Leu
65                  70                  75                  80

Phe Pro His Trp Ile Lys Lys Pro Asn Arg Gln Gly Leu Gly Tyr Tyr
                85                  90                  95

Ser Pro Ser Tyr Asn Asp Pro Cys Ser Leu Gln Cys Pro Tyr Leu Gly
            100                 105                 110

Cys Gln Ser Trp Thr Cys Pro Tyr Thr Gly Pro Val Ser Ser Pro Ser
        115                 120                 125

Trp Lys Phe His Ser Asp Val Asn Phe Thr Gln Glu Val Ser Gln Val
    130                 135                 140

Ser Leu Arg Leu His Phe Ser Lys Cys Gly Ser Ser Met Thr Leu Leu
145                 150                 155                 160

Val Asp Ala Pro Gly Tyr Asp Pro Leu Trp Phe Ile Thr Ser Glu Pro
                165                 170                 175

Thr Gln Pro Pro Pro Thr Ser Pro Pro Leu Val His Asp Ser Asp Leu
            180                 185                 190

Glu His Val Leu Thr Pro Ser Thr Ser Trp Thr Thr Lys Ile Leu Lys
        195                 200                 205

Phe Ile Gln Leu Thr Leu Gln Ser Thr Asn Tyr Ser Cys Met Val Cys
    210                 215                 220

<210> SEQ ID NO 29
<211> LENGTH: 228
<212> TYPE: PRT
<213> ORGANISM: Artificial Sequence
<220> FEATURE:
<223> OTHER INFORMATION: Derived from Env Simian T Leukaemia Virus-3
<220> FEATURE:
<221> NAME/KEY: PEPTIDE
<222> LOCATION: (1)..(228)
```

<400> SEQUENCE: 29

Met Gly Lys Ser Gly Leu Tyr Phe Ser Leu Ile Cys Phe Tyr Thr Leu
1               5                   10                  15

Phe Pro Ser Ser Phe Gly Asn Pro Ser Arg Cys Thr Leu Phe Ile Gly
            20                  25                  30

Ala Ser Ser Tyr His Ser Asp Pro Cys Gly Ser Asn His Pro Arg Cys
        35                  40                  45

Thr Trp Arg Leu Asp Leu Phe Ser Leu Thr Lys Asp Gln Ser Leu Ser
    50                  55                  60

Pro Pro Cys Pro Gly Leu Val Thr Tyr Ser Gln Tyr His Lys Pro Tyr
65                  70                  75                  80

Ser Leu Tyr Val Phe Pro His Trp Ile Ala Lys Pro Asp Arg Arg Gly
                85                  90                  95

Leu Gly Tyr Tyr Ser Ala Ser Tyr Ser Asp Pro Cys Ala Ile Gln Cys
            100                 105                 110

Pro Tyr Leu Gly Cys Gln Ser Trp Thr Cys Pro Tyr Thr Gly Pro Val
        115                 120                 125

Ser Ser Pro His Trp Lys Tyr Thr Ser Asp Leu Asn Phe Thr Gln Glu
    130                 135                 140

Val Ser Ser Ile Ser Leu His Leu His Phe Ser Lys Cys Gly Tyr Ser
145                 150                 155                 160

Phe Ser Phe Leu Leu Asp Ala Pro Gly Tyr Asp Pro Val Trp Leu Leu
                165                 170                 175

Ser Ser Gln Ala Thr Gln Ile Pro Pro Thr Pro Ala Pro Leu Ile Arg
            180                 185                 190

Asp Pro Asp Leu Gln His Ile Leu Glu Pro Ser Ile Pro Trp Ser Ser
        195                 200                 205

Lys Ile Leu Asn Leu Ile Leu Leu Ala Leu Lys Ser Thr Asn Tyr Ser
    210                 215                 220

Cys Met Val Cys
225

<210> SEQ ID NO 30
<211> LENGTH: 215
<212> TYPE: PRT
<213> ORGANISM: Artificial Sequence
<220> FEATURE:
<223> OTHER INFORMATION: Derived from Env Bovine Leukaemia Virus
<220> FEATURE:
<221> NAME/KEY: PEPTIDE
<222> LOCATION: (1)..(215)

<400> SEQUENCE: 30

Met Pro Lys Glu Arg Arg Ser Arg Arg Arg Pro Gln Pro Ile Ile Arg
1               5                   10                  15

Trp Val Ser Leu Thr Leu Thr Leu Leu Ala Leu Cys Gln Pro Ile Gln
            20                  25                  30

Thr Trp Arg Cys Ser Leu Ser Leu Gly Asn Gln Gln Trp Met Thr Thr
        35                  40                  45

Tyr Asn Gln Glu Ala Lys Phe Phe Ile Ser Ile Asp Gln Ile Leu Glu
    50                  55                  60

Ala His Asn Gln Ser Pro Phe Cys Pro Arg Ser Pro Arg Tyr Thr Leu
65                  70                  75                  80

Asp Phe Val Asn Gly Tyr Pro Lys Ile Tyr Trp Pro Pro Gln Gly
                85                  90                  95

```
Arg Arg Arg Phe Gly Ala Arg Ala Met Val Thr Tyr Asp Cys Glu Pro
            100                 105                 110

Arg Cys Pro Tyr Val Gly Ala Asp His Phe Asp Cys Pro His Trp Asp
            115                 120                 125

Asn Ala Ser Gln Ala Asp Gln Gly Ser Phe Tyr Val Asn His Gln Thr
130                 135                 140

Leu Phe Leu His Leu Lys Gln Cys His Gly Ile Phe Thr Leu Thr Trp
145                 150                 155                 160

Glu Ile Trp Gly Tyr Asp Pro Leu Ile Thr Phe Ser Leu His Lys Ile
                165                 170                 175

Pro Asp Pro Pro Gln Pro Asp Phe Pro Gln Leu Asn Ser Asp Trp Val
            180                 185                 190

Pro Ser Val Arg Ser Trp Ala Leu Leu Leu Asn Gln Thr Ala Arg Ala
            195                 200                 205

Phe Pro Asp Cys Ala Ile Cys
            210                 215

<210> SEQ ID NO 31
<211> LENGTH: 224
<212> TYPE: PRT
<213> ORGANISM: Artificial sequence
<220> FEATURE:
<223> OTHER INFORMATION: Derived from Env Human T Leukaemia Virus-4
<220> FEATURE:
<221> NAME/KEY: PEPTIDE
<222> LOCATION: (1)..(224)

<400> SEQUENCE: 31

Met Gly Asn Val Leu Phe Leu Thr Leu Leu Ala Thr Leu Gly Ile Pro
1               5                   10                  15

Val Leu Gln Ala Ser Arg Cys Thr Ile Thr Val Gly Ile Ser Ser Tyr
            20                  25                  30

His Ser Ser Pro Cys Ser Pro Ala Gln Pro Leu Cys Thr Trp Ala Leu
            35                  40                  45

Asp Leu Val Ser Ile Thr Lys Asp Gln Leu Leu Tyr Pro Pro Cys Gln
50                  55                  60

Asn Leu Ile Thr Tyr Ser Asn Tyr His Lys Thr Tyr Ser Leu Tyr Leu
65                  70                  75                  80

Phe Pro His Trp Val Gln Lys Pro Leu Arg Arg Gly Leu Gly Tyr Tyr
                85                  90                  95

Ser Ala Ser Tyr Ser Asp Pro Cys Ser Leu Gln Cys Pro Tyr Leu Gly
            100                 105                 110

Ser Gln Ser Trp Thr Cys Pro Tyr Thr Gly Pro Val Ser Ser Pro Thr
            115                 120                 125

Trp Arg Phe Ser Thr Asp Val Asn Phe Thr Gln Glu Val Ser Arg Val
            130                 135                 140

Ser Leu Lys Leu His Phe Ser Lys Cys Gly Ser Ser Leu Thr Leu Leu
145                 150                 155                 160

Ile Asp Ala Pro Gly Tyr Asp Pro Leu Trp Tyr Leu Thr Ser Glu Pro
                165                 170                 175

Thr Gln Glu Pro Pro Thr Pro Pro Leu Val Ser Asp Ser Asp Leu
            180                 185                 190

Glu His Val Leu Thr Pro Ser Ala Ser Trp Ala Ser Lys Met Leu Thr
            195                 200                 205

Leu Ile His Leu Thr Leu Gln Ser Thr Asn Tyr Ser Cys Met Val Cys
210                 215                 220
```

METHOD FOR THE DIAGNOSIS AND/OR PROGNOSIS OF GRANULOCYTE-RELATED INFLAMMATORY STATES

FIELD OF THE INVENTION

The invention relates to a method for the diagnosis and/or prognosis of inflammatory states.

BACKGROUND OF THE INVENTION

Virus receptor-binding domain (RBD) are found in particular in the envelope glycoprotein (Env) of viruses and are able to bind to membrane receptors of different target cells.

Gamma and deltaretroviruses have been shown to interact with cell surface through active receptors that belong to the multimembrane protein family. Those receptors for which a function has been identified (or most certainly those with no identified function) are directly involved in cellular metabolism.

Retroviral envelope-derived probes, which can be used for specific, high-affinity tagging of metabolic transporters on human cells, have been disclosed in WO 2010/079208. These transporters carry a wide variety of metabolites, including, but not limited to: neutral amino acids (AA), cationic AA, glucose, heme and vitamins.

Retroviral envelope-derived probes of WO 2010/079208 have been used for the detection of membrane receptors present in a target cell such as haematopoietic stem cells, such as CD34 cells, or differentiated cells such as B-cells or T-cells.

Myelocyte and monocyte lines (granulocytes) play a major role in body's response to stress. During infestation by pathogens, regulated signals by epithelial and inflammatory cells get position to coordinate innate and acquired immunity. A rapid intervention is necessary and involves a complete reprogramming of quiescent circulating myelocyte and monocyte lines to be activated and migrate to injury sites. This turn over, requiring gene transcription and protein production, is energy-dependent. It needs nutrients and metabolites absorption that can be reflected with an increase of metabolic transporters at the surface of inflammatory cells.

Asthma is a chronic disease characterized by bronchoconstriction, wheezing, cough and breath difficulties during exacerbations. This pathology affects about 300 million worldwide. The airway inflammation is generated by an influx of myelocyte and monocyte lines in the lungs; mostly eosinophils seem to be implied as well as neutrophils.

Allergy is also a disorder of the immune system caused by the suractivation of mast cells and basophils when they identify allergen-specific immunoglobulin IgE. Activated cells release histamine and cytokines maintaining and aggravating the reaction of inflammation. Allergic crisis could manifest minor symptoms but also serious reactions as respiratory difficulties and coma.

Cystic fibrosis (also known as CF) is a common disease which affects the entire body, causing progressive disability and often early death.

Difficulty breathing is the most serious symptom and results from frequent lung infections that are treated, though not cured, by antibiotics and other medications. A multitude of other symptoms, including sinus infections, poor growth, diarrhea, and infertility result from the effects of CF on other parts of the body.

The increasing importance of these pathologies makes the discovery of a rapid detection of them or of therapeutical agents highly desirable.

One of the aims of the present invention is to provide RBD for the detection of membrane receptors present in granulocytes indicating an inflammatory state.

Another aim of the invention is to provide a diagnosis and/or prognosis process of an inflammation state.

Still another aim of the invention is to provide a method for measuring the therapeutic efficacy of a potential anti-inflammatory drug in a mammal.

SUMMARY OF THE INVENTION

The present invention relates to the use of at least one soluble receptor-binding domain (RBD), for the identification and quantification of the expression of membrane receptors present on the surface of target granulocytes, said identification and quantification taking place at a given time or during a given time interval, and allowing the diagnosis and/or prognosis of inflammatory states in a mammal.

By receptor-binding domain (RBD) is meant a functional fragment (or a part) of a glycoprotein contained in the envelope of a virus so long it retains some or all of the binding properties of the RBD to a membrane receptor present on the surface of target granulocytes, and can be obtained for example by cloning.

By the expression "soluble receptor binding domain" is meant a soluble functional fragment (or a part) of a glycoprotein contained in the envelope of a virus so long it retains some or all of the binding properties of the RBD to a membrane receptor present on the surface of target granulocytes, and can be obtained for example by cloning.

One or more amino acids can be added to, deleted, or substituted from the RBD sequence of this fragment or part of glycoprotein so long it retains the ability to bind to a membrane receptor present on the surface of target granulocytes.

By the term "glycoprototein" is meant an envelope glycoprotein, a coat glycoprotein or a fusion glycoprotein.

Said part or fragment or totality of the RBD of the glycoprotein of the virus is liable to bind to or interact with one or more membrane receptor(s) of a target granulocyte.

The expression "liable to bind or to interact with at least one or more membrane receptor(s)" means that said part or fragment or totality of the RBD forms a complex with a receptor of the target granulocyte or to several receptors of the target granulocyte.

The complex may thus be formed in vitro in the case where the target granulocytes have been previously isolated from an animal.

The complex can also be formed ex vivo.

The complex can also be formed in vivo in the case where the RBD is injected to an animal and interact with the target granulocytes in the animal organism.

By "membrane receptor" it is defined in the invention any protein or polypeptide anchored in the plasma membrane of cells. Said membrane receptor allows the interaction with glycoprotein of viruses.

Preferably the membrane receptors according to the invention are members of the multimembrane-spanning protein family which functions as transporters, such as nutriment and metabolite transporters, i.e. multimembrane-spanning proteins that allow the transport of nutriments and metabolites across the plasma membrane. (RBD and receptors are described in FIG. 1).

By "target granulocyte" is meant a cell belonging to myelocyte or monocyte lines and presenting a distinctive array of receptors anchored within the membrane of the cell.

The "target granulocyte" can be isolated from an animal, and is for example a mammalian granulocyte, in particular neutrophils, eosinophils, basophils and mast cells, preferably during an inflammation state.

The expression "identification and the quantification of the expression of membrane receptors present on the surface of target granulocyte" means that when a target granulocyte expresses a membrane receptor, i.e. said receptor is present on the surface of the target granulocyte, therefore a complex is formed between the membrane receptor of a biological interest target granulocyte and RBD.

That complex can be detected if the RBD has been for instance, but without being limited to, covalently coupled with a detectable molecule such as an antibody constant fragment (Fc) or a fluorescent compound (cyanins, alexa, quantum dots . . . )

That complex can also be detected if the RBD has been tagged with different means well known by a person skilled in the art.

For instance, but without limitations, the tag used in the invention can be Hemaglutinin Tag, Poly Arginine Tag, Poly Histidine Tag, Myc Tag, Strep Tag, Flag Tag, S-Tag, HAT Tag, 3× Flag Tag, Calmodulin-binding peptide Tag, SBP Tag, Chitin-binding domain Tag, GST Tag, Maltose-Binding protein Tag, GFP and EGFP Tag, RFPs Tag, YFP Tag, CFP Tag, T7 tag, V5 tag, Xpress tag and all fluorescent molecules having an emission maximum comprised from 445 nm to 655 nm available from Olympus America inc.

The use of a RBD allows therefore on the one hand the identification of the receptor expressed on the target granulocyte depending on the RBD used and on the other hand the quantification of the complex formed, and thus the presence or not of a membrane receptor on the target granulocyte and its quantification.

The expression "at a given time or during a given time interval" means that the detection and/or the quantification of the complex formed can be made just after the contacting of the RBD and the membrane receptor of the target granulocyte or after several minutes, in particular from 1 to 59 minutes, or several hours, in particular from 1 to 47 h, preferably 24 h, or days, in particular from 2 to 7 days, preferably 3 days, or several weeks, preferably 3 to 6 weeks when evaluating decay of said membrane receptors on the target granulocyte, after said contacting, depending on the cells and the contacting conditions, in order to evaluate the modification of the expression of membrane receptors.

Contacting conditions include also the temperature that can vary from 0° C. to 37° C., in particular 0, 1, 2, 3 or 4° C., preferably near room temperature, in particular from 18° C. to 25° C., in particular 18, 19, 20, 21, 22, 23, 24 or 25° C., more preferably from 26 to 37° C., in particular 25, 26, 27, 28, 29, 30, 31, 32, 33, 34, 35, 36, or 37° C., preferably 30 or 37° C. depending on the target granulocytes.

By "inflammation state" is meant acute or chronic inflammation occurring during allergy, asthma, acne vulgaris, autoimmune diseases, chronic prostatitis, glomerulonephritis, hypersensitivities, inflammatory bowel diseases, pelvic inflammatory disease, reperfusion injury, rheumatoid arthritis, sarcoidosis, transplant rejection, vasculitis, interstitial cystitis, or cystic fibroses.

In an advantageous embodiment, said inflammatory state is an inflammation of the respiratory tract.

The invention thus allows, by using the receptor binding domains defined above, the identification and quantification of particular expressed receptors at the surface of granulocytes cells, indicating an inflammatory state of said granulocytes, said expressed receptors being not expressed or expressed in a lesser extent in normal conditions, and therefore allowing the diagnosis and/or the prognosis of pathologies in which an inflammatory state is implicated such as pathologies defined above.

DETAILED DESCRIPTION OF THE INVENTION

In an advantageous embodiment, the present invention relates to the use of at least one soluble receptor-binding domain (RBD) as defined above, for the identification and quantification of the expression of membrane receptors present on the surface of target granulocytes, said identification and quantification taking place at a given time or during a given time interval, and allowing the diagnosis and/or prognosis of inflammatory states, provided that when only one RBD is used, said membrane receptor is not GLUT1.

In this embodiment, when one RBD is used for the identification and quantification of the expression of membrane receptors present on the surface of target granulocytes for the diagnosis and/or prognosis of inflammatory states, then said membrane receptor identified and quantified is not GLUT1. In other words, said membrane receptor is a membrane receptor other than GLUT1.

Said inflammatory states can be as defined above or in particular, inflammation of the respiratory tract.

In an advantageous embodiment, the present invention relates to the use of at least one soluble receptor-binding domain (RBD) as defined above, wherein said at least one soluble receptor-binding domain is a set of three to twenty soluble receptor-binding domains, preferably a set of three to twelve soluble receptor-binding domain in particular three, four, five, six seven, eight, nine, ten, eleven, or twelve receptor-binding domain.

In this embodiment, three to up to twenty RBD are used, depending of the number of receptors being present at the surface of the cell.

Each RBD recognizes at least one membrane receptor.

That means that each RBD of said set can interact either with only one receptor, or with two or more distinct receptors, and that two or more RBDs can interact with the same membrane receptor or with two or more distinct receptors.

Whatever the number of RBD used, if several RBD are used, each RBD can recognize the same receptor named $R_1$ for example, or two or more distinct receptors $R_1$ and $R_2$ for example, or more than two distinct receptors $R_1$ to $R_n$ (n>3) for example, the receptors recognized by each RBD being the same or different.

Therefore, in this embodiment, all the combinations between the three to twenty RBD and the membrane receptors are included.

In an advantageous embodiment, the present invention relates to the use of at least one soluble receptor-binding domain (RBD) as defined above, wherein said at least one soluble receptor-binding domain is a set of three to twenty soluble receptor-binding domain, preferably a set of three to twelve soluble receptor-binding domain in particular three, four, five, six seven, eight, nine, ten, eleven, or twelve receptor-binding domain, provided that at least one soluble receptor-binding domain of said set does not interact with GLUT1 membrane receptor.

In this embodiment, each RBD recognizes at least one membrane receptor and each membrane receptor is recognized by at least one RBD.

That means that each RBD of said set can interact either with the same receptor, but in this case at least one soluble receptor-binding domain of said set does not interact with GLUT1 membrane receptor, that is at least one soluble receptor-binding domain of said set interacts with a membrane receptor other than GLUT1, or with two or more distinct receptors.

Therefore, in this embodiment, all the combinations between the three to twenty RBD and the membrane receptors are included provide that at least one soluble receptor-binding domain of said set interacts with a membrane receptor other than GLUT1.

The upper limit of the number of RBD is only due to the method used to detect the formed complex, i.e. by Fluorescence Activated Cell Sorting (FACS) the number of channels of which is at present time limited to twenty but it could be higher than twenty with other methods.

In an advantageous embodiment, the present invention relates to the use of at least one soluble receptor-binding domain (RBD) as defined above, wherein said target granulocytes are selected from, the list consisting of neutrophils, eosinophils, basophils and mast cells.

Neutrophil granulocytes are generally referred to as either neutrophils or polymorphonuclear neutrophils (or PMNs) and form an essential part of the innate immune system.

Neutrophils are normally found in the blood stream. However, during the beginning (acute) phase of inflammation, neutrophils are one of the first-responders of inflammatory cells to migrate toward the site of inflammation, firstly through the blood vessels, then through interstitial tissue.

Basophil granulocytes, also referred to as basophils, are the least common of the granulocytes. Basophils appear in many specific kinds of inflammatory reactions, particularly those that cause allergic symptoms.

Eosinophil granulocytes, usually called eosinophils, are one of the immune system components responsible for combating multicellular parasites and certain infections in vertebrates Along with mast cells, they also control mechanisms associated with allergy and asthma.

Mast cells play a key role in the inflammatory process. When activated, a mast cell rapidly releases its characteristic granules and various hormonal mediators into the interstitium. Mast cells can be stimulated to degranulate by direct injury (e.g. physical or chemical [such as opioids, alcohols, and certain antibiotics such as polymyxins]).

In an advantageous embodiment, said membrane receptors can be chosen among, but without being limited to, CAT1, PiT2, XPR1, SMIT1, Plasmolipin, PiT1, ASCT1, ASCT2, FLVCR, feTHTR1, PAR, GLUT1.

The above mentioned membrane receptors are disclosed in Manel et al. Frontiers in Bioscience, 9, 3218-3241, 2004.

PAR has been identified as PAR 1 (or hRFT3) (GenBank accession no. NM_024531) and PAR2 (or hRFT1).

Said membrane receptor can also be an unidentified receptor the complex of which with a RBD can be identified and quantify in order to identify and quantify the expression of said receptor at the surface of target granulocytes.

In an advantageous embodiment, the present invention relates to the use of at least one soluble receptor-binding domain (RBD) as defined above, wherein said target, granulocytes are neutrophils and said inflammatory state is that found in patients with cystic fibrosis.

In a particularly advantageous embodiment, for the cystic fibrosis, if said RBD is AMLV, it must then be associated with at least one other RBD.

Cystic fibrosis (also known as CF) is a common disease which affects the entire body, causing progressive disability and often early death.

Difficulty breathing is the most serious symptom and results from frequent lung infections that are treated, though not cured, by antibiotics and other medications. A multitude of other symptoms, including sinus infections, poor growth, diarrhea, and infertility result from the effects of CF on other parts of the body.

In an advantageous embodiment, the present invention relates to the use of at least one soluble receptor-binding domain (RBD) as defined above, wherein said neutrophils are blood neutrophils or lung neutrophils.

Airway disease in cystic fibrosis (CF) is due to the massive recruitment of blood polymorphonuclear neutrophils (PMN) into lungs. PMN in this context have been shown to go through an anabolic reprogramming suspected to be due to a complete change of metabolic physiology.

One of the advantages of the invention is to characterize these changes of metabolic physiology, with receptor-binding domain (RBD) of retrovirus envelope glycoproteins (Env) liable to bind transporters directly linked to cell metabolism.

In an advantageous embodiment, the present invention relates to the use of at least one soluble receptor-binding domain (RBD) as defined above, wherein said target granulocytes are eosinophils and said inflammatory state is allergy and/or asthma.

As previously indicated, the airway inflammation is generated by an influx of myelocyte and monocyte lines in the lungs; mostly eosinophils seem to be implied as well as neutrophils.

The identification and quantification of membrane receptors expressed on eosinophils and/or neutrophils is thus of interest in the diagnosis and/or prognosis of allergy and/or asthma and/or the follow up of a treatment against these ailments.

In an advantageous embodiment, the present invention relates to the use of at least one soluble receptor-binding domain (RBD) as defined above, wherein said target granulocytes are basophils and said inflammatory state is allergy.

In an advantageous embodiment, the present invention relates to the use of at least one soluble receptor-binding domain (RBD) as defined above, wherein said target granulocytes are masts and said inflammatory state is allergy.

Allergy is also a disorder of the immune system caused by the suractivation of mast cells and/or basophils when they identify allergen-specific immunoglobulin IgE.

The identification and quantification of membrane receptors expressed on eosinophils and/or masts is thus of interest in the diagnosis and/or prognosis of allergy.

In an advantageous embodiment, the present invention relates to the use of at least one soluble receptor-binding domain (RBD) as defined above, wherein said RBD is selected from the list consisting of: SEQ ID NO: 1 to 31.

The SEQ IDs 1 to 31 are constituted of the signal peptide when known, the receptor binding domain, the proline rich region (PRR) when known and the CXXC motif located downstream of the PRR.

The list comprising SEQ IDs 1 to 31 defined above is not limitative and can be extended to all the RBD that can be found in a mammal.

In an advantageous embodiment, the present invention relates to the use of at least one soluble receptor-binding domain (RBD) as defined above, wherein said RBD is selected from the list consisting of: Amphotropic Murine Leukemia Retrovirus (AMLV, SEQ ID NO:1), Feline endogenous retrovirus (RD114, SEQ ID NO:3), Koala endogeneous Retrovirus (KoRV, SEQ ID NO: 20), Human T Leukaemia Virus-2 (HTLV2, SEQ ID NO: 28), Bovine Leukaemia Virus (BLV, SEQ ID NO: 30), or Porcine Endogeneous Retrovirus-A (Perv A, SEQ ID NO: 21).

Depending on the granulocytes implied in said pathology, one RBD can be enough to identify and quantify the membrane receptors expressed on said granulocyte, but in some cases, two or more RBD are necessary to carry out said identification and quantification.

Thus, single RBD or combinations of RBD of examples 3 to 5 are used as examples only and it is obvious that other single RBD or combinations of RBD can be used for identification and quantification of the expression of membrane receptors present on the surface of target granulocytes.

Therefore, in one embodiment, the invention discloses the use as defined above, wherein said RBD is Amphotropic Murine Leukemia Retrovirus (AMLV, SEQ ID NO:1).

In another embodiment, the invention discloses the use as defined above, wherein said RBD is Feline endogenous retrovirus (RD114, SEQ ID NO:3).

In another embodiment, the invention discloses the use as defined above, wherein said RBD is Koala endogeneous Retrovirus (KoRV, SEQ ID NO: 20).

In another embodiment, the invention discloses the use as defined above, wherein said RBD is Human T Leukaemia Virus-2 (HTLV2, SEQ ID NO: 28).

In another embodiment, the invention discloses the use as defined above, wherein said RBD is Bovine Leukaemia Virus (BLV, SEQ ID NO: 30).

In another embodiment, the invention discloses the use as defined above, wherein said RBD is Porcine Endogeneous Retrovirus-A (Perv A, SEQ ID NO: 21).

In another embodiment, the invention discloses the use as defined above, wherein said RBD is a combination of two soluble RBD selected from the list consisting of: Amphotropic Murine Leukemia Retrovirus (AMLV, SEQ ID NO:1), Feline endogenous retrovirus (RD114, SEQ ID NO:3), Koala endogeneous Retrovirus (KoRV, SEQ ID NO: 20), Human T Leukaemia Virus-2 (HTLV2, SEQ ID NO: 28), Bovine Leukaemia Virus (BLV, SEQ ID NO: 30), or Porcine Endogeneous Retrovirus-A (Perv A, SEQ ID NO: 21).

In another embodiment, the invention discloses the use as defined above, wherein said RBD is a combination of three soluble RBD selected from the list consisting of: Amphotropic Murine Leukemia Retrovirus (AMLV, SEQ ID NO:1), Feline endogenous retrovirus (RD114, SEQ ID NO:3), Koala endogeneous Retrovirus (KoRV, SEQ ID NO: 20), Human T Leukaemia Virus-2 (HTLV2, SEQ ID NO: 28), Bovine Leukaemia Virus (BLV, SEQ ID NO: 30), or Porcine Endogeneous Retrovirus-A (Perv A, SEQ ID NO: 21).

In another embodiment, the invention discloses the use as defined above, wherein said RBD is a combination of four soluble RBD selected from the list consisting of: Amphotropic Murine Leukemia Retrovirus (AMLV, SEQ ID NO:1), Feline endogenous retrovirus (RD114, SEQ ID NO:3), Koala endogeneous Retrovirus (KoRV, SEQ ID NO: 20), Human T Leukaemia Virus-2 (HTLV2, SEQ ID NO: 28), Bovine Leukaemia Virus (BLV, SEQ ID NO: 30), or Porcine Endogeneous Retrovirus-A (Perv A, SEQ ID NO: 21).

In another embodiment, the invention discloses the use as defined above, wherein said RBD is a combination of five soluble RBD selected from the list consisting of: Amphotropic Murine Leukemia Retrovirus (AMLV, SEQ ID NO:1), Feline endogenous retrovirus (RD114, SEQ ID NO:3), Koala endogeneous Retrovirus (KoRV, SEQ ID NO: 20), Human T Leukaemia Virus-2 (HTLV2, SEQ ID NO:28), Bovine Leukaemia Virus (BLV, SEQ ID NO: 30), or Porcine Endogeneous Retrovirus-A (Perv A, SEQ ID NO:21).

In another embodiment the invention discloses the use as defined above, wherein said RBD is a combination of six soluble RBD selected from the list consisting of: Amphotropic Murine Leukemia Retrovirus (AMLV, SEQ ID NO:1), Feline endogenous retrovirus (RD114, SEQ ID NO:3), Koala endogeneous Retrovirus (KoRV, SEQ ID NO: 20), Human T Leukaemia Virus-2 (HTLV2, SEQ ID NO:28), Bovine Leukaemia Virus (BLV, SEQ ID NO: 30), or Porcine Endogeneous Retrovirus-A (Perv A, SEQ ID NO:21).

In an advantageous embodiment, the present invention relates to the use of at least one soluble receptor-binding domain (RBD) as defined above, wherein said at least one soluble receptor-binding domain is a combination of two soluble receptor-binding domain (RBD).

In an advantageous embodiment, at least one of said soluble receptor-binding domain of said combination does not interact with GLUT1 membrane receptor, that is at least one soluble receptor-binding domain of said combination interacts with a membrane receptor other than GLUT1.

The following combinations of two RBD illustrate said both embodiments (with and without the proviso concerning GLUT1) without limiting the invention and other combinations of two RBDs can be under the scope of the present invention.

Amphotropic Murine Leukemia Retrovirus (AMLV, SEQ ID NO:1) and Feline endogenous retrovirus (RD114, SEQ ID NO:3), Amphotropic Murine Leukemia Retrovirus (AMLV, SEQ ID NO:1) and Koala endogeneous Retrovirus (KoRV, SEQ ID NO: 20), Amphotropic Murine Leukemia Retrovirus (AMLV, SEQ ID NO:1) and Human T Leukaemia Virus-2 (HTLV2, SEQ ID NO: 28), Amphotropic Murine Leukemia Retrovirus (AMLV, SEQ ID NO:1) and Bovine Leukaemia Virus (BLV, SEQ ID NO: 30), Amphotropic Murine Leukemia Retrovirus (AMLV, SEQ ID NO:1) and Porcine Endogeneous Retrovirus-A (Perv A, SEQ ID NO: 21), Feline endogenous retrovirus (RD114, SEQ ID NO:3) and Koala endogeneous Retrovirus (KoRV, SEQ ID NO: 20), Feline endogenous retrovirus (RD114, SEQ ID NO:3) and Human T Leukaemia Virus-2 (HTLV2, SEQ ID NO: 28), Feline endogenous retrovirus (RD114, SEQ ID NO:3) and Bovine Leukaemia Virus (BLV, SEQ ID NO: 30), Feline endogenous retrovirus (RD114, SEQ ID NO:3) and Porcine Endogeneous Retrovirus-A (Perv A, SEQ ID NO: 21), Koala endogeneous Retrovirus (KoRV, SEQ ID NO: 20) and Human T Leukaemia Virus-2 (HTLV2, SEQ ID NO: 28), Koala endogeneous Retrovirus (KoRV, SEQ ID NO: 20) Bovine Leukaemia Virus (BLV, SEQ ID NO: 30), Koala endogeneous Retrovirus (KoRV, SEQ ID NO: 20) Porcine Endogeneous Retrovirus-A (Perv A, SEQ ID NO: 21).

Human T Leukaemia Virus-2 (HTLV2, SEQ ID NO: 28) and Bovine Leukaemia Virus (BLV, SEQ ID NO: 30).

In an advantageous embodiment, the present invention relates to the use of at least one soluble receptor-binding domain (RBD) as defined above, wherein said combination is the combination of HTLV-2 RBD (SEQ ID NO: 28) and KoRV RBD (SEQ ID NO: 20) and said membrane receptors are GLUT1 and PiT1 respectively, said membrane receptors being expressed in particular in lung neutrophils and blood neutrophils.

In an advantageous embodiment, the present invention relates to the use of said combination of HTLV-2 RBD (SEQ ID NO: 28) and KoRV RBD (SEQ ID NO: 20) as defined above, wherein the expression of said membrane receptors in lung neutrophils is increased compared with the expression of said membrane receptor in blood neutrophils.

In an advantageous embodiment, the present invention relates to the use of at least one soluble receptor-binding domain (RBD) as defined above, wherein said soluble receptor binding domains are a combination of RD114 RBD (SEQ ID NO:3) and AMLV RBD (SEQ ID NO:1) and said membrane receptors are ASCT2 and PiT2 respectively.

In an advantageous embodiment, the present invention, relates to the use of said combination of RD114 RBD (SEQ ID NO:3) and AMLV RBD (SEQ ID NO:1) as defined above, wherein the expression of one or both said membrane receptors in lung neutrophils is increased or decreased compared with the expression of said membrane receptors in blood neutrophils.

In an advantageous embodiment, the present invention relates to the use of at least one soluble receptor-binding domain (RBD) as defined above, wherein said combination is the combination of PERVA RBD (SEQ ID NO: 21) and BLV RBD (SEQ ID NO: 30) and said membrane receptors are PAR and a membrane receptor interacting with BLV respectively, said membrane receptors being potentially expressed in particular in lung neutrophils and blood neutrophils.

PERVA RBD can interact with PAR1 (hRFT3) and PAR2 (hRFT1).

In an advantageous embodiment, the present invention relates to the use of at least one soluble receptor-binding domain (RBD) as defined above, wherein the expression of said PAR membrane receptor m lung neutrophils is decreased compared with the expression of said membrane receptor in blood neutrophils and said receptor interacting with BLV in lung neutrophils is increased compared with the expression of said membrane receptor in blood neutrophils.

In another aspect, the present invention relates to a process of diagnosis and/or prognosis of an inflammatory state in a mammal, comprising the identification and quantification of the expression of at least one membrane receptors, said identification and quantification being as defined as defined above, present on the surface of target granulocytes.

In an advantageous embodiment the present invention relates to a process of in vitro diagnosis and/or prognosis of an inflammatory state in a mammal, as defined above, wherein the target granulocytes have been previously isolated from a mammal.

In an advantageous embodiment the present invention relates to a process of ex vivo diagnosis and/or prognosis of an inflammatory state in a mammal, as defined above.

In an advantageous embodiment the present invention relates to a process of ex vivo diagnosis and/or prognosis of an inflammatory state in a mammal, as defined above, and/or of follow up of an anti-inflammatory treatment.

In an advantageous embodiment the present invention relates to a process of in vivo diagnosis and/or prognosis of an inflammatory state in a mammal, as defined above.

In this embodiment, the RBD is injected to a mammal and interact with the target granulocytes in the mammal organism, the identification and quantification of the expression of at least one membrane receptors being carried out on the surface of target granulocytes of said mammal.

In an advantageous embodiment the present invention relates to a process of in vivo diagnosis and/or prognosis of an inflammatory state in a mammal, as defined above, and/or of follow up of an anti-inflammatory treatment.

In an advantageous embodiment, the present invention relates to a process of diagnosis and/or prognosis of an inflammatory state in a mammal, comprising the identification and quantification of the expression of at least one membrane receptors, said identification and quantification being as defined above, present on the surface of target granulocytes, provided that when only one RBD is used, said membrane receptor is not GLUT1, and when two or more RBD are used, at least one of said soluble receptor-binding domain does not interact with GLUT1 membrane receptor.

In an advantageous embodiment, the present invention relates to a process of diagnosis and/or prognosis of an inflammatory state in a mammal, comprising the identification and quantification of the expression of at least one membrane receptors, as defined above, and/or of follow up of an anti-inflammatory treatment.

In an advantageous embodiment the present invention relates to a process of in vitro diagnosis and/or prognosis of an inflammatory state in a mammal, as defined above, wherein when only one RBD is used, said membrane receptor is not GLUT1, i.e. said membrane receptor is a membrane receptor other than GLUT1, and when two or more RBD are used, at least one of said soluble receptor-binding domain does not interact with GLUT1 membrane receptor, i.e. at least one soluble receptor-binding domain interacts with a membrane receptor other than GLUT1.

In an advantageous embodiment the present invention relates to a process of ex vivo diagnosis and/or prognosis of an inflammatory state in a mammal, as defined above, wherein when only one RBD is used, said membrane receptor is not GLUT1, i.e. said membrane receptor is a membrane receptor other than GLUT1, and when two or more RBD are used, at least one of said soluble receptor-binding domain does not interact with GLUT1 membrane receptor, i.e. at least one soluble receptor-binding domain interacts with a membrane receptor other than GLUT1.

In an advantageous embodiment the present invention relates to a process of ex vivo diagnosis and/or prognosis of an inflammatory state in a mammal, as defined above, and/or of follow up of an anti-inflammatory treatment, wherein when only one RBD is used, said membrane receptor is not GLUT1, i.e. said membrane receptor is a membrane receptor other than GLUT1, and when two or more RBD are used, at least one of said soluble receptor-binding domain does not interact with GLUT1 membrane receptor, i.e. at least one soluble receptor-binding domain interacts with a membrane receptor other than GLUT1.

In an advantageous embodiment the present invention relates to a process of in vivo diagnosis and/or prognosis of an inflammatory state in a mammal, as defined above, and/or of follow up of an anti-inflammatory treatment wherein when only one RBD is used, said membrane receptor is not GLUT1, i.e. said membrane receptor is a membrane receptor other than GLUT1, and when two or more RBD are used, at least one of said soluble receptor-binding domain does not interact with GLUT1 membrane receptor, i.e. at least one soluble receptor-binding domain interacts with a membrane receptor other than GLUT1.

In an advantageous embodiment, the present invention relates to a process of diagnosis and/or prognosis of an inflammatory state in a mammal, as defined above, comprising the following steps:

a. contacting at least one soluble receptor-binding domain, as defined above, optionally marked with a tag, with target granulocytes of a diseased mammal to form at least one complex, said at least one complex being constituted by said at least one soluble receptor-binding domain and at least one membrane receptor of said target granulocytes,
b. identifying said at least complex formed,
c. quantifying the expression of each membrane receptor of said target granulocytes able to form said complex, d. contacting said at least one soluble receptor-binding domain of step a. with target granulocytes of a control mammal and identifying each complex formed as in step b. and quantifying the expression of each membrane receptor of said target granulocytes able to form said complex as in step c.

e. comparing the level of expression of membrane receptors in step c and d, an overexpression or underexpression of membrane receptors of target granulocytes of said diseased mammal compared with control mammal indicating an inflammatory state.

In this embodiment, granulocytes of a healthy mammal that has no inflammatory state is the control of the process.

Granulocytes of an untreated diseased mammal can also be the control of the process.

In an advantageous embodiment, the present invention relates to a process of diagnosis and/or prognosis of an inflammatory state in a mammal, as defined above, and/or of follow up of an anti-inflammatory treatment.

In an advantageous embodiment, the present invention relates to a process of diagnosis and/or prognosis of an inflammatory state in a mammal, as defined above, and/or of follow up of an anti-inflammatory treatment comprising a further step of comparing the level of expression of membrane receptors in steps c and d above defined, an overexpression or underexpression of membrane receptors of target granulocytes of said diseased mammal under treatment compared with untreated controls indicating a modification of the inflammatory state.

In this embodiment, granulocytes of a healthy mammal that has no inflammatory state or an untreated diseased mammal are the control of the process.

Tags used are as defined above and identification of the complexes formed are carried out as described above.

The contact of at least one soluble receptor-binding domain, as defined above, optionally marked with a tag, with target granulocytes of a diseased mammal, treated and/or untreated, or of a control mammal is comprised from about 15 min to about 45 min and in particular 30 min at a temperature as defined above.

In this embodiment, the overexpression or the underexpression of one membrane receptor of a diseased mammal compared with the expression of said membrane receptor in a control mammal is a specific biomarker of inflammation.

In an advantageous embodiment, the process of diagnosis and/or prognosis of an inflammatory state in a mammal, defined above, comprises a step a. wherein two RBD are used as specific biomarker of inflammation.

In an advantageous embodiment, the process of diagnosis and/or prognosis of an inflammatory state in a mammal, defined above, comprises a step a, wherein three RBD are used as specific biomarker of inflammation as specific biomarker of inflammation.

In an advantageous embodiment, the process of diagnosis and/or prognosis of an inflammatory state in a mammal, defined above, comprises a step a. wherein four RBD are used as specific biomarker of inflammation.

In an advantageous embodiment, the process of diagnosis and/or prognosis of an inflammatory state in a mammal, defined above, comprises a step a. wherein five RBD are used as specific biomarker of inflammation.

In an advantageous embodiment, the process of diagnosis and/or prognosis of an inflammatory state in a mammal, defined above, comprises a step a. wherein six RBD are used as specific biomarker of inflammation.

In an advantageous embodiment, the process of diagnosis and/or prognosis of an inflammatory state in a mammal, defined above, comprises a step a. wherein seven to twenty RBD are used as specific biomarker of inflammation.

In an advantageous embodiment, the present invention relates to a process of diagnosis and/or prognosis of an inflammatory state in a mammal, wherein said control mammal is the same mammal species as the diseased mammal.

In this embodiment, granulocytes of said diseased mammal that has an inflammatory state is also the control of the process.

In an advantageous embodiment, the present invention relates to a process of diagnosis and/or prognosis of an inflammatory state in a mammal, wherein said granulocytes are neutrophils, in particular blood neutrophils and lung neutrophils.

Thus in this embodiment, blood PMNs (quiescents) that have been sampled from each patients, at the same time, are the control of lung PMN (activated).

Nevertheless, patient group having a level of inflammation significantly different from patient groups with higher level of inflammation can also be considered as controls group (see Example 2).

In an advantageous embodiment, the present invention relates to a process of diagnosis and/or prognosis of an inflammatory state in a mammal, as defined above, wherein the inflammatory state is cystic fibrosis.

In an advantageous embodiment, the present invention relates to a process of diagnosis and/or prognosis of an inflammatory state in a mammal, as defined above, comprising the following steps:

a. contacting HTLV-2 RBD (SEQ ID NO: 28) and/or KoRV RBD (SEQ ID NO: 20), optionally marked with a tag, with lung neutrophils of a mammal to form at least one complex, b. identifying said at least one complex formed and being constituted by HTLV-2 receptor-binding domain and GLUT1 membrane receptor and/or KoRV receptor-binding domain and PiT1 membrane receptor of said lung neutrophils, c. quantifying the expression of said GLUT1 and/or PiT1 membrane receptor of said lung neutrophils able to form said complex, d. contacting said HTLV-2 RBD and/or KoRV RBD with blood neutrophils and identifying and quantifying the expression of said GLUT1 and/or PiT1 membrane receptor of said blood neutrophils able to form said complex, e. comparing the level of expression of each membrane receptor, an over expression of GLUT1 and/or PiT1 in lung neutrophils compared with blood neutrophils indicating a pulmonary inflammatory state during cystic fibrosis.

In an advantageous embodiment, the present invention relates to a process of diagnosis and/or prognosis of an inflammatory state in a mammal, as defined above, comprising the following steps:

a. contacting RD114 RBD (SEQ ID NO:3) and AMLV RBD (SEQ ID NO:1), optionally marked with a tag, with lung neutrophils of a mammal to form at least one complex, b. identifying said at least one complex formed and being constituted by RD114 receptor-binding domain and ASCT2 membrane receptor and/or AMLV receptor-binding domain and PiT2 membrane receptor of said lung neutrophils, c. quantifying the expression of said ASCT2 and/or PiT2 membrane receptor of said lung neutrophils able to form said complex,
d. contacting said RD114 RBD and/or AMLV RBD with blood neutrophils and identifying and quantifying the expression of said ASCT2 and/or PiT2 membrane receptor of said blood neutrophils able to form said complex,
e. comparing the level of expression of each membrane receptor, an overexpression and/or underexpression of ASCT2 and/or PiT2 in blood neutrophils compared with lung neutrophils indicating a pulmonary inflammatory state during cystic fibrosis.

The level of expression of both receptors (ASCT2 and PiT2) is a biomarker of a severe pulmonary inflammatory state during cystic fibrosis.

In an advantageous embodiment, the present invention relates to a process of diagnosis and/or prognosis of an inflammatory state in a mammal, as defined above, comprising the following steps:
a. contacting PERVA RBD (SEQ ID NO: 21) and and/or BLV RBD (SEQ ID NO: 30) optionally marked with a tag, with lung neutrophils of a mammal to form at least one complex,
b. identifying said at least one complex formed and being constituted by PERVA receptor-binding domain and PAR membrane receptor of said lung neutrophils, and/or BLV receptor-binding domain and a membrane receptor interacting with BLV,
c. quantifying the expression of said PAR and/or a membrane receptor interacting with BLV of said lung neutrophils able to form said complex,
d. contacting said PERVA RBD and/or BLV RBD with blood neutrophils and identifying and quantifying the expression of each said PAR and/or a membrane receptor interacting with BLV of said blood neutrophils able to form said complex,
e. comparing the level of expression of each membrane receptor, an overexpression of said membrane receptor interacting with BLV in blood neutrophils compared with lung neutrophils and/or an underexpression of PAR in blood neutrophils compared with lung neutrophils indicating a pulmonary inflammatory state during cystic fibrosis.

In an advantageous embodiment, the process of diagnosis and/or prognosis of an inflammatory state in a mammal defined above comprised a step a. wherein three RBD, are used as specific biomarkers of CF.

Table I specifies all the combinations of three RBD that can be used:

TABLE I

|  | HTLV-2 | KoRV | RD114 | AMLV | PERVA | BLV |
|---|---|---|---|---|---|---|
| Combinations of three RBD | X | X | X |  |  |  |
|  | X | X |  | X |  |  |
|  | X | X |  |  | X |  |
|  | X | X |  |  |  | X |
|  | X |  | X | X |  |  |
|  | X |  | X |  | X |  |
|  | X |  | X |  |  | X |
|  | X |  |  | X | X |  |
|  | X |  |  | X |  | X |
|  | X |  |  |  | X | X |
|  |  | X | X | X |  |  |
|  |  | X | X |  | X |  |
|  |  | X | X |  |  | X |
|  |  | X |  | X | X |  |
|  |  | X |  | X |  | X |

TABLE I-continued

|  | HTLV-2 | KoRV | RD114 | AMLV | PERVA | BLV |
|---|---|---|---|---|---|---|
|  | X |  |  |  | X | X |
|  |  | X | X | X |  |  |
|  |  | X | X |  |  | X |
|  |  | X |  |  | X | X |
|  |  |  |  | X | X | X |

In an advantageous embodiment, the process of diagnosis and/or prognosis of an inflammatory state in a mammal defined above comprised a step a. wherein four RBD are used as specific biomarker of CF.

Table II specifies all the combinations of four RBD that can be used:

TABLE II

|  | HTLV-2 | KoRV | RD114 | AMLV | PERVA | BLV |
|---|---|---|---|---|---|---|
| Combinations of four RBD | X | X | X | X |  |  |
|  | X | X | X |  | X |  |
|  | X | X | X |  |  | X |
|  | X | X |  | X | X |  |
|  | X | X |  | X |  | X |
|  | X | X |  |  | X | X |
|  | X |  | X | X | X |  |
|  | X |  | X | X |  | X |
|  | X |  | X |  | X | X |
|  |  | X | X | X | X |  |
|  |  | X | X | X |  | X |
|  |  | X | X |  | X | X |
|  |  | X |  | X | X | X |
|  |  |  | X | X | X | X |
|  | X |  |  | X | X | X |

In an advantageous embodiment, the process of diagnosis and/or prognosis of an inflammatory state in a mammal defined above comprised a step a. wherein five RBD are used as specific biomarker of CF.

Table III specifies all the combinations of five receptor RBD that can be used:

TABLE III

|  | HTLV-2 | KoRV | RD114 | AMLV | PERVA | BLV |
|---|---|---|---|---|---|---|
| Combinations of five RBD | X | X | X | X | X |  |
|  | X | X | X | X |  | X |
|  | X |  | X | X | X | X |
|  | X | X |  | X | X | X |
|  | X | X | X |  | X | X |
|  |  | X | X | X | X | X |

In an advantageous embodiment, the process of diagnosis and/or prognosis of an inflammatory state in a mammal defined above comprised a step a. wherein six RBD such as HTLV-2/KoRV/RD114/AMLV/BLV/PERVA are used as specific biomarker of CF.

The processes according to the invention defined above show that overexpression and/or underexpression membrane receptors of target granulocytes expressed in lung neutrophils compared with blood neutrophils, and identified and quantified by of one, two, three four, five or six RBD or more (up to twenty) are specific biomarkers of an inflammatory state during cystic fibrosis.

In an advantageous embodiment, the present invention relates to a process of diagnosis and/or prognosis of an inflammatory state in a mammal, as defined above, wherein said granulocytes are eosinophils.

In an advantageous embodiment, the present invention relates to a process of diagnosis and/or prognosis of an inflammatory state in a mammal, as defined above, wherein said granulocytes are basophils.

In an advantageous embodiment, the present invention relates to a process of diagnosis and/or prognosis of an inflammatory state in a mammal, as defined above, wherein said granulocytes are mast cells.

In another aspect, the present invention relates to a method for measuring the therapeutic efficacy of a potential anti-inflammatory drug in a mammal, comprising the following steps:
  a. identifying and quantifying the expression of at least one membrane receptor, said identification and quantification being as defined in claim 1, present on the surface of target granulocytes,
  b. contacting said granulocytes with a drug liable to treat said inflammatory state to give treated granulocytes,
  c. identifying and quantifying the expression of at least one membrane receptor as defined in claim 1, present on the surface of treated granulocytes,
  d. comparing the level of expression of said at least one membrane receptor before and after contacting with said drug, an increase and/or a decrease of the expression of said at least one membrane receptor after contacting indicating a therapeutic efficacy of said drug depending of said inflammatory state.

In an advantageous embodiment the present invention relates to a method for in vitro measuring the therapeutic efficacy of a potential anti-inflammatory drug in a mammal, or a drug that leads to a drop of granulocyte counts in body fluids, comprising the step a. to d. defined above, wherein the target granulocytes have been previously isolated from a mammal.

In an advantageous embodiment the present invention relates to a method for ex vivo measuring the therapeutic efficacy of a potential anti-inflammatory drug in a mammal, or a drug that leads to a drop of granulocyte counts in body fluids, comprising the step a. to d. defined above.

In an advantageous embodiment the present invention relates to a method for in vivo measuring the therapeutic efficacy of a potential anti-inflammatory drug in a mammal, or a drug that leads to a drop of granulocyte counts in body fluids, comprising the step a. to d. defined above, wherein the RBD is injected to a mammal and interact with the target granulocytes in the mammal organism, and the drug liable to treat said inflammatory state is injected to a mammal, the identification and quantification of the expression of at least one membrane receptors being carried out on the surface of target granulocytes of said mammal.

In an advantageous embodiment the present invention relates to methods for measuring the therapeutic efficacy of a potential anti-inflammatory drag in a mammal, or a drug that leads to a drop of granulocyte counts in body fluids, as defined above, wherein step a. is carried out provided that when only one RBD is used, said membrane receptor is not GLUT1, i.e. said membrane receptor is a membrane receptor other than GLUT1, and when two or more RBD are used, at least one of said soluble receptor-binding domain does not interact with GLUT1 membrane receptor, i.e. at least one soluble receptor-binding domain interacts with a membrane receptor other than GLUT1.

In an advantageous embodiment, anti-inflammatory drug identified above, can be used for the preparation of a drug intended for the treatment of inflammatory states, such as cystic fibrosis, allergy or asthma.

Figure 3:
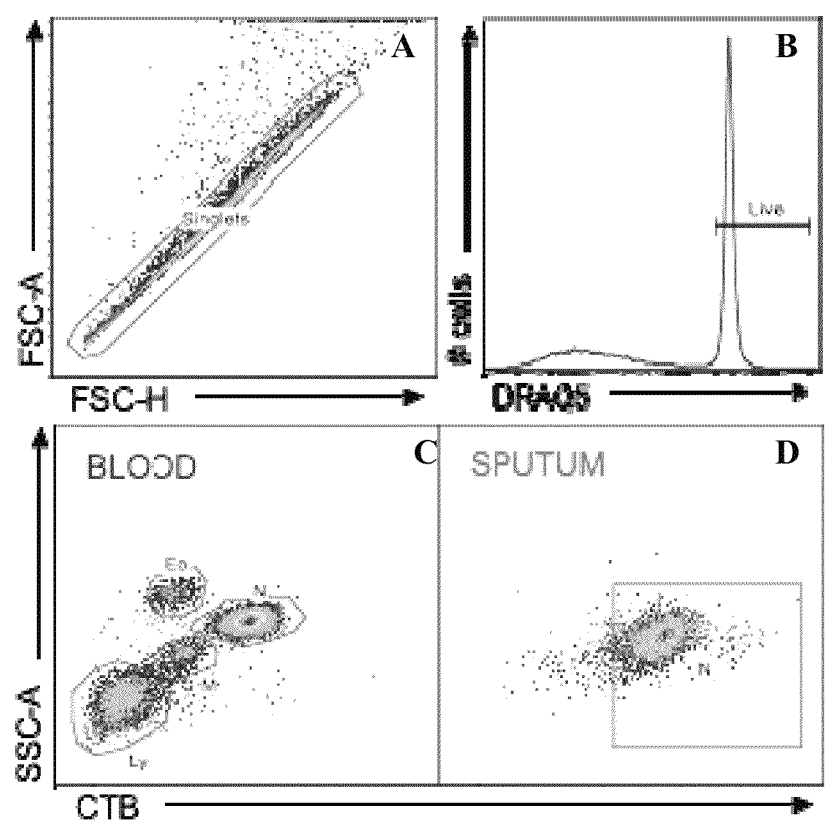
FIG. 3A to 3D present the gating strategy for population discrimination.

Typically, single live neutrophils are gated via two analytical gates, as depicted on the upper left panel (FIGS. 3A and 3B).

Then subpopulations of blood leucocytes (Eo: eosinophils, Ly: Lymphocytes, M: monocytes and N: neutrophils) are discriminated and airways neutrophils (N) are selected with CTB staining, down left panel (PMN are $CTB^{hi}/SSC-A^{hi}$) (FIGS. 3C and 3D).

FSC-A: Forward light scatter-area

SSC-A: Side light scatter-area

FSC-H: Forward light scatter-Height

CTB: Cholera Toxin B

DRAQ5™: marker of cell viability.

Figure 4:
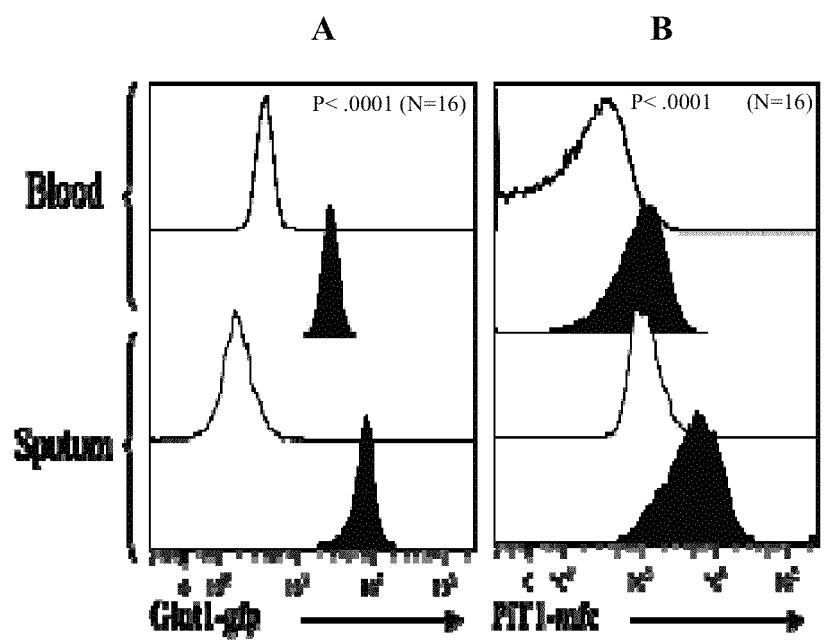
Figure 5:
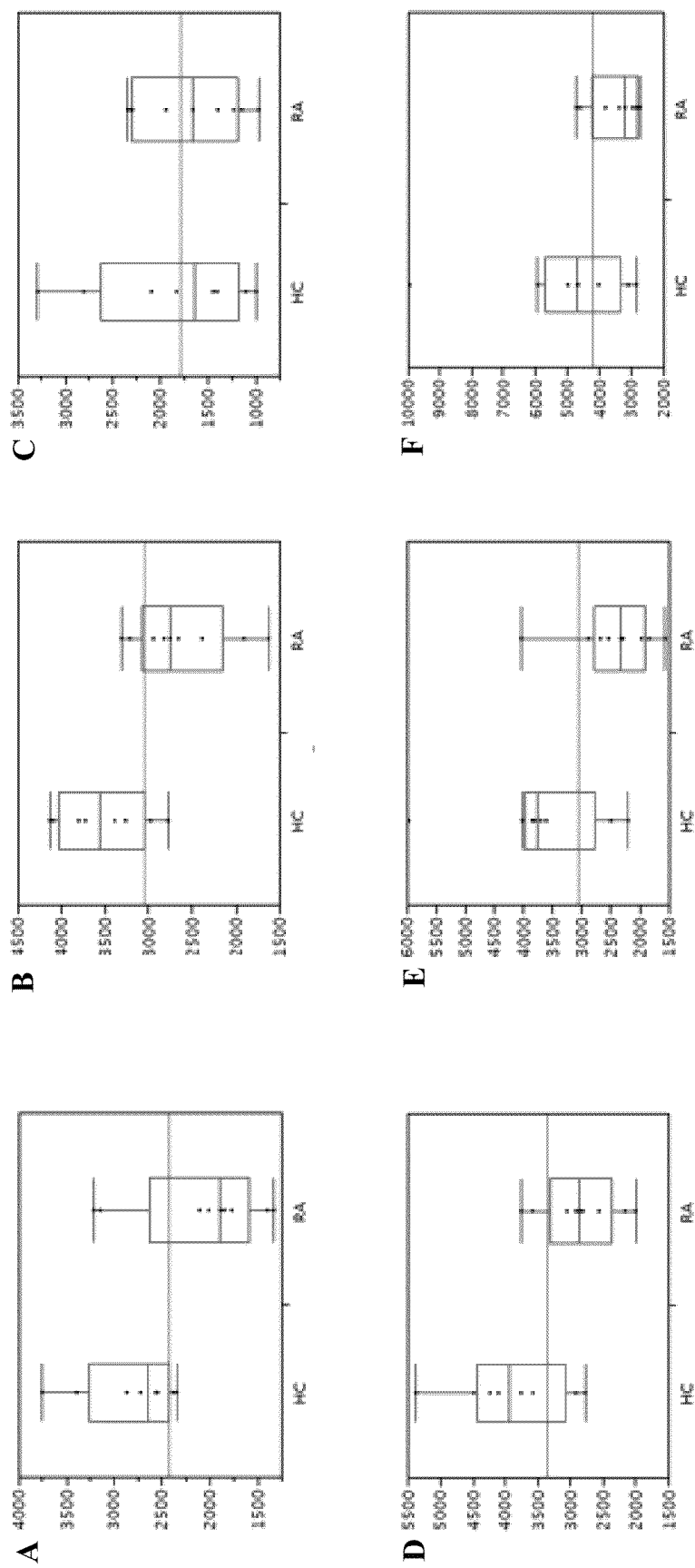

FIGS. 4A and 4B present the RBD binding and transporter expression.

FIG. 4A present the expression of GLUT1 in Blood neutrophils (upper half, upper unfilled curve corresponding to the mock and black filled curve correspond to the binding of GLUT1) and in Sputum neutrophils (lower half upper unfilled curve corresponding to the mock and black filled curve corresponding to the binding of GLUT1).

FIG. 4B present the expression of PiT1 in Blood neutrophils (upper half, upper unfilled curve corresponding to the mock and black filled curve correspond to the binding of PiT1) and in Sputum neutrophils (lower half, upper unfilled curve corresponding to the mock and black filled curve corresponding to the binding of PiT1).

Measures (Geomean of fluorescence) of Glut1, PiT1 on gated CF PMN. Statistical analyses are performed with the Wilcoxon test. Histograms on left are representative of 16 patients for Glut1 and PiT1 expression.

FIGS. 5A to 5F present the RBD binding and transporters expression on neutrophils from rheumatoid arthritis patients (RA) and healthy control donors (HC). Measures (deltaMedian of fluorescence) of PiT1 (FIG. 5A), PiT2 (FIG. 5D), BLV receptor (FIG. 5B), hRFT1 &3 (FIG. 5E), ASCT2 (FIG. 5C) and Glut1 (FIG. 5F) on gated RA and HC PMN. Statistical analyses are performed with the Wilcoxon test. Graphs are representative of 8 HC and 9 RA patients.

EXAMPLES

Example 1

General Method for the Productions of Receptor Binding Ligands with 293T Cells Transfection At D-1: 293T Cells Spreading

| Plate type | 6 wells | 60 mm | 10 cm |
| --- | --- | --- | --- |
| Cell numbers | $3 \times 10^5$ | $10^6$ | $2 \times 10^6$ |

At D0: Transfection by Calcium Phosphate Precipitation

| Plate type  | 6 wells | 60 mm | 10 cm |
|---|---|---|---|
| Volume (ml) | 3 ml    | 5 ml  | 10 ml |

1) Prepare the HBS+DNA of a receptor binding protein in an eppendorf tube (under hood):

| Plate type           | 6 wells | 60 mm | 10 cm |
|---|---|---|---|
| DNA total quantity (µg) | 6       | 10    | 20    |
| PCSI                 | 6       | 10    | 20    |
| Vol. HBS (µl)        | 150     | 250   | 500   |

2) Add CaCl2 2M (sterile) up to a final concentration=125 mM:

| Plate type      | 6 wells | 60 mm | 10 cm |
|---|---|---|---|
| Vol. CaCl2 2M (µl) | 10      | 17    | 33    |

3) "Gently" Vortex for 10 sec,
4) Incubate 5 min at RT, a white precipitate is formed,
5) Gently add the precipitate on cells and homogenise,
6) Put the cells inside the incubator (37° C., 5% CO2).

At D1: Medium Change;
The sooner the possible in the morning and gently (293T cells detach easily) with 10 ml of optipro SFM Medium (Gibco) without FBS—16H MAX,
Then incubate (32° C., 5% CO2).

After 48 h, i.e. at D3: Supernatant Recovering and Concentration
Recover the conditioned medium in 50 ml falcon tube
Spin at 1500 tr/min, 3 min, 4° C.
Filter the supernatant on 0.45 µm
Conserve the supernatant on ice
Add 20 ml of ultrapure water in the concentrators (Icon concentrator, 20 ml/9 k, PIERCE)
Spin at 3600 tr/min, 10 min, (Swinging-bucket), 4° C.
Add 20 ml of filtered RBD sample
Spin at 3600 tr/min, 20 min, 4° C.
Add sample, centrifuge 20 min (100 ml max of RBD for each concentrator)
Spin until desired concentration factor is achieved (100×)
Recover concentrated sample, aliquot and stock at −80° c.

Example 2

General Method of FACS

The FACS assay of HRBD-EGFP (non antibody Glut1-ligand) is representative of the method for the receptors binding ligands:
Target cells: Any mammalian cell lines/human RBC/Human activated PBLs or any subpopulation/any primary or established cell type of interest.
For the binding assay: Entire binding assay should be performed on ice except for the actual binding step performed at 37° C.
RBD stored at −80° C.
Thaw RBD-containing conditioned medium, and mock transfected conditioned medium. Avoid re-freezing the RBD preparation.

Single Assay in Eppendorf Tubes
1-2×10$^5$ cells per assay in 1.5 ml eppendorf tube
Centrifuge 3 mm at 3200 RPM.
Aspirate supernatant gently.
Gently resuspend pellet (tapping)
Dilute the concentrated HRBD-EGFP 1/20 (v/v) dilution in PBS or medium
Add 100 µl to 200 µl/tube of the dilution and resuspend gently.
Incubate 30 min at 37° C. (no agitation is required).
Keep cold during all the following steps
Centrifuge 3 min at 3200 RPM 4° C., gently aspirate supernatant and gently tap pellet.
Add 1 ml of cold PBA (PBS+2% FBS and 0.01% sodium azide) and gently top pellet.
Repeat last two steps, resuspend pellet with 500 µl of PBA and transfer to FACS tubes
FACS analysis Multiple Assays in 96 Well-Microplates (V Bottom)
1-2×10$^5$ cells for each binding assay per well.
Centrifuge 3 min at 1500 RPM.
Discard the supernatant by quickly flipping the plate (over sink for instance).
Place the plate upside down on absorbing paper to eliminate remaining droplets.
Gently vortex the plate.
Dilute the concentrated HRBD-EGFP preparation 1/20 (v/v) in PBS or medium.
Add 50 µl/well of the diluted preparation of HRBD-EGFP and resuspend gently.
Incubate 30 min at 37° C. (no agitation is required).
Transfer to 4° C. for ail the following steps.
Centrifuge 3 min at 1500 RPM at 4° C. and discard supernatant as previously.
Wash pellet with 200 µl of cold PBA twice, with 3 min centrifuge at 1500 RPM.
Resuspend pellet with 200 µl of PBA and transfer the mix to FACS tubes.
FACS analysis Example 3

HTLV-2 and KoRV RBDs as Markers of CF in Blood and Lung Neutrophils

Figure 1:
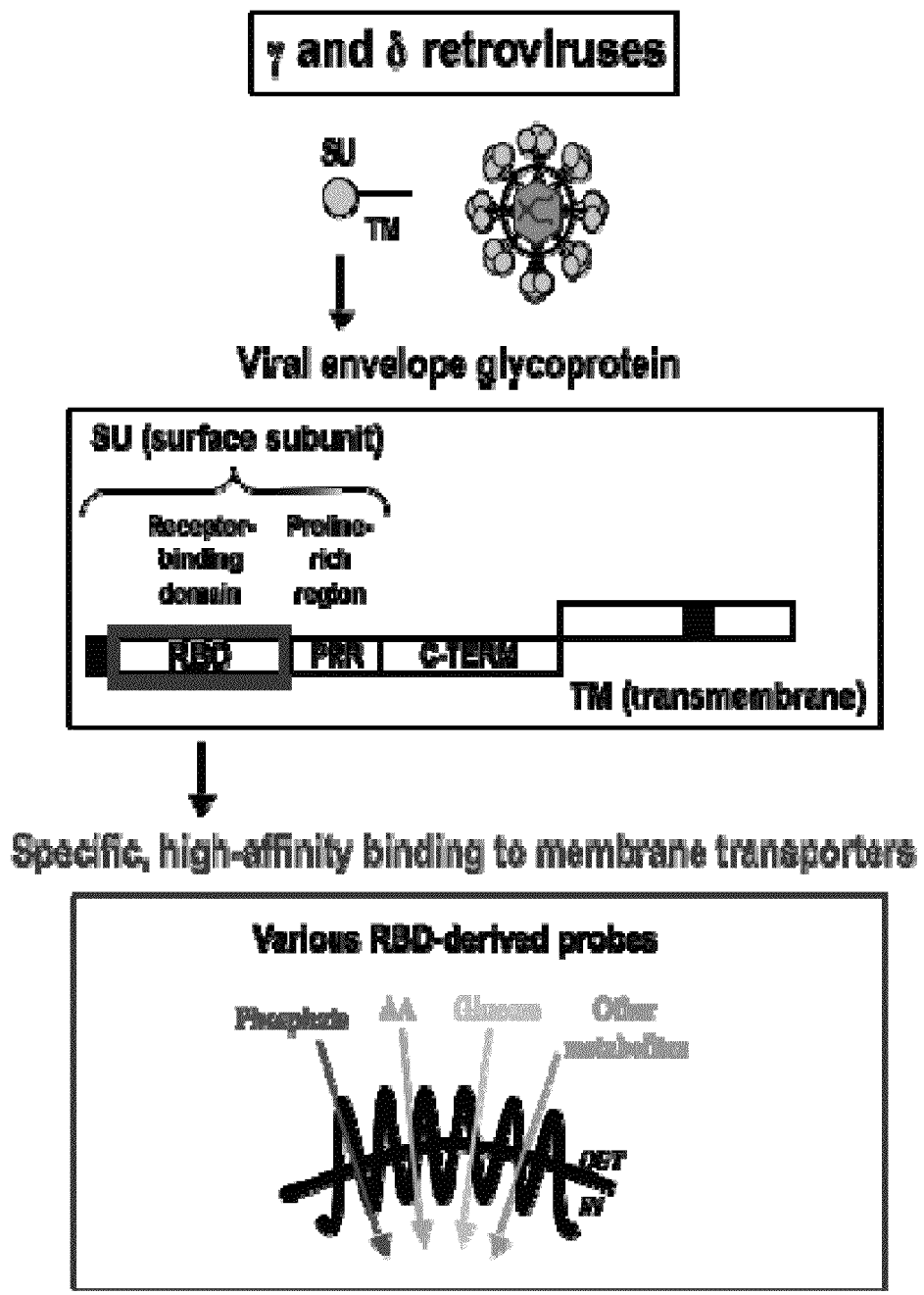
FIG. 1 presents the localization of a receptor-binding domain (RBD or RBD-derived probes) from γ and δ viral Receptor-Binding Domain (RBD) of envelope glycoprotein (Env) which will be inserted in a vector plasmid.
Figure 2:
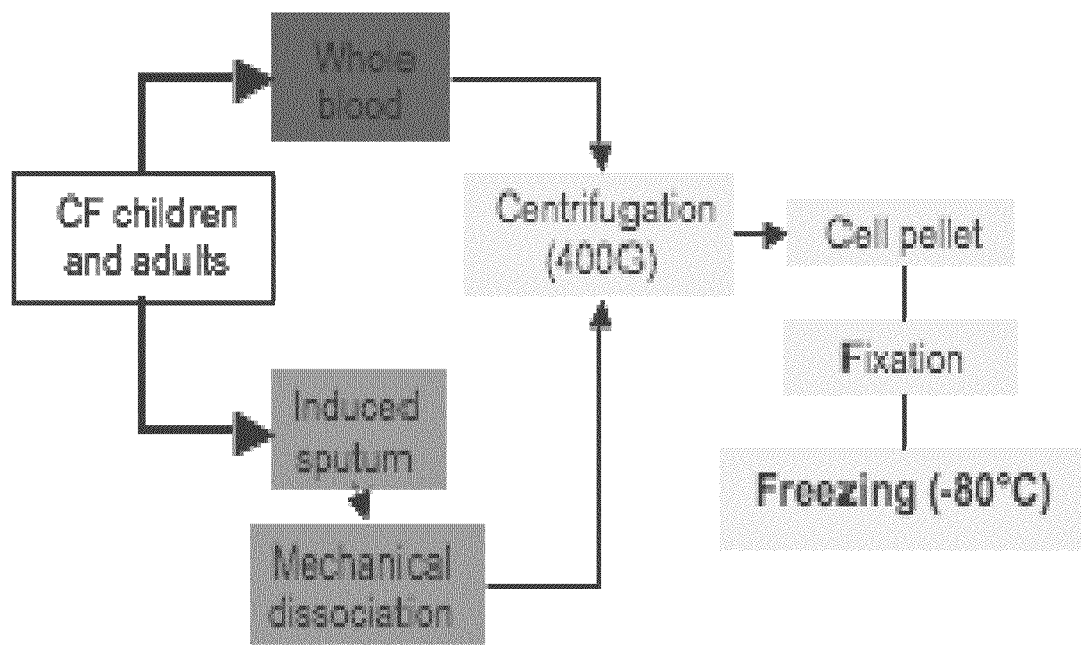
FIG. 2 presents the sample processing in CF. Both blood and sputum are collected from children and adults, centrifuged at 400 g to pellet cells, which are fixed and then frozen at −80° C. until analyze.

To use soluble RBD, a protocol requiring few experimental steps until flow cytometry measures was elaborated.
In brief, HTLV-2 RBD/KoRV RBD were mixed together to obtained a combination of probes. Cells (~250.10$^3$, blood and sputum neutrophils, see FIG. 2) are incubated with this combination holding tagged-RBD either with EGFP, mouse-IgG Fc or rabbit-IgG Fc. The latters required a secondary stain, with a specific antibody to the particular Fc to be detected (Anti-mouse Fc Alexa Fluor®405 conjugate and/or Anti-rabbit Fc Alexa Fluor® 488 conjugate; both from MOLECULAR PROBES® by Invitrogen™).
In the same time a conjugate of Cholera Toxin 6 (CTB, Alexa Fluor® 555 conjugate; MOLECULAR PROBES® by Invitrogen™) was added that allowed to differentiate leucocyte subpopulations in blood and define neutrophil population m sputum during analyze.
Then, cells were permeabilized with saponin (or Perm/Wash Buffer I; BD™Phosflow; BD Biosciences) and a marker of cell viability (DRAQ5; AXXORA® PLATFORM; Biostatus Limited) was introduced. Assays were running on LSRII cytometer 4-laser LSRII digital FACS (BD™ flow cytometer; BD Biosciences)

Results are presented on table IV.

TABLE IV

|  | Blood | Sputum |
|---|---|---|
| Glut1 | 2634.5 [2150.5; 3096] | 4392 [3672.5; 5207.5] |
| Pit1 | 594 [328.25; 881.7] | 2483 [2138.25; 3378.5] |

Data show deltaGeomean of fluorescence by Median and Interquartile range [25%; 75%].

Table IV is representative of 16 patients for Glut1 and PiT1 expression.

It must be noted that:

HTLV-2 RBD or KoRV RBD used in example 3 could have been used alone as specific biomarkers of PMN activation in CF, and a combination of two RBD: HTLV-2/AMLV or HTLV-2/RD114 or KoRV/AMLV or KoRV/RD114 would have lead to similar diagnosis/prognosis of inflammation.

Example 4

RD114 and AMLV RBDs as Markers of CF in Blood and Lung Neutrophils

To use soluble RBD, a protocol requiring few experimental steps until flow cytometry measures was elaborated.

In brief, RD114 RBD/AMLV RBD were mixed together to obtained a combination of probes. Cells (~250.10$^3$, blood and sputum neutrophils, see FIG. 2) are incubated with this combination holding tagged-RBD either with EGFP, mouse-IgG Fc or rabbit-IgG Fc. The latters required a secondary stain with a specific antibody to the particular Fc to be detected.

In the same time a conjugate of Cholera Toxin B (CTB) was added that allowed to differentiate leucocyte subpopulations in blood and define neutrophil population in sputum during analyze.

Then, cells were permeabilized with saponin and a marker of cell viability (DRAQ5) was introduced. Assays were running on LSRII cytometer.

Results are presented on table V: Characterization of CF inflammation by airway PMN count, ASCT2 and PiT2 expression.

Patients (N=16) are divided in 3 groups considering airway PMN quantity (PMN/mL). ASCT2 and Pit2 level expression data are classified according to the comparison between blood (B) and sputum (S). Values represent deltaGeomean of fluorescence by Median and Interquartile range [25%; 75%].

This analyze showed that a combined overexpression of ASCT2 and PiT2 in blood when compared to sputum (B≥S) correlates with the most elevated airway PMN counts (superior or equal to 12.10$^5$ cells), corresponding to a high level of inflammation.

Moreover, it could be concluded that a combined expression of ASCT2 and PiT2 in blood PMN comprised within a deltaGeomean range of [605; 1272] and [28.7; 36.2] (×10$^3$), respectively, is predictive of the highest inflammation level (N=5).

It must be noted that in this example, use of AMLV RBD alone is not enough to allow a diagnosis of inflammation contrary to RD114 RBD alone with which the difference between (B<S) and (B≥S) is higher.

It must also be noted that RBD of examples 3 and 4 can be combined.

As an example, a combination of three RBD described in example 3 and 4: HTLV-2/KoRV/RD114 or HTLV-2/KoRV/AMLV or HTLV-2/RD114/AMLV or KoRV/RD114/AMLV, or a combination of four RBD; HTLV-2/KoRV/RD114/AMLV would have lead to more specific biomarkers of PMN activation in CF, in particular a severe pulmonary inflammatory state during cystic fibrosis, and a more precise diagnosis and/or prognosis of inflammation.

Example 5

PERVA and BLV RBDs as Markers of CF in Blood and Lung Neutrophils

To use soluble RBD, a protocol requiring few experimental steps until flow cytometry measures was elaborated.

In brief, PERV A RBD/BLV RBD were mixed together to obtained a combination of probes, or used separetely. Cells (~250.10$^3$, blood and sputum neutrophils, see FIG. 2) are incubated with this combination holding tagged-RBD either with EGFP, mouse-IgG Fc or rabbit-IgG Fc. The latters required a secondary stain with a specific antibody to the particular Fc to be detected.

In the same time a conjugate of Cholera Toxin B (CTB) was added that allowed to differentiate leucocyte subpopulations in blood and define neutrophil population in sputum during analyze.

Then, cells were permeabilized with saponin and a marker of cell viability (DRAQ5) was introduced. Assays were running on LSRII cytometer Results are presented on table VI: PervA and BLV RBDs binding. DeltaGeomean of fluorescence measures on one patient samples.

TABLE V

| Airway PMN Count (n/mL) | ASCT2 | | FiT2 (×10$^3$) | |
|---|---|---|---|---|
|  | B < S | B ≥ S | B < S | B ≥ S |
| <3 · 10$^6$ (180 · 10$^3$ – 2.25 · 10$^6$) | B = 556 [52; 1138] S = 1652 [1327; 2027] (N = 4) | — | B = 22 [16.4; 23.9] S = 37 [20.6; 42.1] (N = 3) | B = 35.5 S = 32.7 (N = 1) |
| 3 · 10$^6$ ≤ n < 12 · 10$^6$ (3.1 · 10$^6$ – 6.9 · 10$^6$) N = 6 | B = 474 [257; 752] S = 1763 [1122; 2170] (N = 6) | — | B = 20.3 [16; 25.8] S = 43.5 [23.4; 48.4] (N = 3) | B = 35.5 [27; 37.4] S = 31.1 [12.7; 34] (N = 3) |
| ≥12 · 10$^6$ (12.7 · 10$^6$ – 49 · 10$^6$) N = 6 | B = 192 S = 1747 (N = 1) | B = 1011 [605; 1272] S = 580 [518; 900] (N = 5) | B = 18.8 S = 33.7 (N = 1) | B = 32.9 [28.7; 36.2] S = 17.2 [14.2; 23.4] (N = 5) |

PERVA RBD, derived from the porcine endogenous retrovirus A, binds PAR (for PeRV A Receptor) receptors, including the human Riboflavin Transporter 1 (hRFT1 or PAR2) and hRFT3 (or PAR1), was tested in a single patient and allowed to see a down regulation of its cognate receptors on airway neutrophils.

Some of the RBDs are probes for not yet identified transporters.

BLV RBD, derived from Bovine Leukemia Virus has been used to see if it was differentially expressed between blood and airway PMN.

BLV RBD has been shown to reveal a receptor that is an activation marker of T and B lymphocytes (Lavanya et al J. Immunol. 2008 Jul. 15, 181(2): 891-8) but has not been described on granulocytes.

Results obtained from one patient showed a higher binding on CF pulmonary activated neutrophils, evidencing the relevance of BLV RBD as a specific biomarker of PMN activation in CF.

TABLE VI

| (N = 1) | Blood | Sputum |
|---|---|---|
| PerVA PAR1 hRFT1 (PAR2) | 4161 | 284 |
| BLV Unknown | 0 | 140 |

Example 5 shows that PAR1 (hRFT3) and PAR2 (bRFT1) on airway PMN in patients is downregulated in the sputum compared to the blood and that the receptor interacting with BLV is overexpressed m sputum compared to blood. In the tested patient, the receptor interacting with BLV has not been detected in blood but it cannot be said that this receptor is not present at all in blood neutrophils.

It must be noted that said receptor interacting with BLV used alone can be relevant as a specific biomarker of PMN activation in CF.

Coupling of the information given by BLV RBD or PERVA RBD and one or more RBD of examples 3 and 4 would have lead to more specific biomarkers of PMN activation m CF and a more precise diagnosis and/or prognosis of inflammation.

Example 6

RBDs as Markers of Asthma and/or Allergy in Blood and Lung Eosinophils

Example 6 show that overexpression and/or underexpression membrane receptors of target granulocytes expressed in lung eosinophils compared with blood eosinophils and identified and quantified by of one, two, three four, five or six RBD are specific biomarkers of allergy and/or asthma.

Example 7

RBDs as Markers of Allergy in Blood and Lung Basophils

Example 7 show that overexpression and/or underexpression membrane receptors of target granulocytes expressed in lung basophils compared with blood basophils and identified and quantified by of one, two, three four, five or six RBD are specific biomarkers of allergy.

Example 8

RBDs as Markers of Allergy in Blood and Lung Mast Cells

Example 8 show that overexpression and/or underexpression membrane receptors of target granulocytes expressed in lung mast cells compared with blood mast cells and identified and quantified by of one, two, three four, five or six RBD are specific biomarkers of allergy.

Example 9

RBDs as Markers of RA Inflammatory State in Blood Neutrophils

The same protocol as in example 3 to 5 has been carried out using KoRV, AMLV, BLV, PERVA, RD114 and HTLV2 RBD to determine the binding and transporter expression (respectively PiT1, PiT2, BLVR, hRFT1&3, ASCT2 and Glut1) on neutrophils from rheumatoid arthritis patients (RA) and healthy control donors (HC).

Results are presented on table VII and figure:

TABLE VII

| | PiT1 | PiT2 | BLVR | hRFT1&3 | ASTC2 | Glut1 |
|---|---|---|---|---|---|---|
| HC | 2637 | 3928 | 3551 | 3738 | 1632 | 4671 |
| | [2417; 3257] | [3076; 4424] | [3039; 4017] | [2764; 3965] | [1170; 2622] | [3313; 5681] |
| RA P | 1883 | 2858 | 2746 | 2322 | 1651 | 3184 |
| (HC ≠ RA) | [1581; 2622] | [2362; 3313] | [2139; 3070] | [1898; 2769] | [1181; 2291] | [2795; 4198] |
| | 0.0209 | 0.0161 | 0.0053 | 0.0433 | NS | NS |

RA patients (N = 9) show an increase in PiT1, PiT2, BLVR and hRFT1&3 expression compare to HC (N = 8).
Values represent deltaMedian of fluorescence by Median and Interquartile range [25%; 75%]

The invention claimed is:

1. A method allowing for the diagnosis and/or prognosis of a granulocyte-related inflammatory state in a subject mammal by the identification and quantification of an increase or a decrease in the expression of membrane receptors present on the surface of target granulocytes, the method comprising:

contacting target granulocytes from said subject mammal with at least one soluble receptor-binding domain (RBD) selected from the group consisting of SEQ ID NO: 1, 3, 20, 21, 28 and 30, wherein said target granulocytes are selected from the group consisting of blood neutrophils, lung neutrophils, eosinophils, basophils and mast cells, and detecting a binding or interaction between the granulocytes and the at least one RBD, wherein, identifying and quantifying an increase in at least one of membrane GLUT1, Pit1, Pit2, and ASCT2 expression in blood neutrophils as compared to lung neutrophils, or identifying and quantifying a decrease in at least one of membrane PAR1 (hRFT3) and PAR2 (hRFT1) in lung neutrophils as compared to blood neutrophils, is indicative of a granulocyte-related inflammatory state, or an exacerbation of the granulocyte-related inflammatory state, in cystic fibrosis; and wherein identifying and quantifying an increase in at least one of membrane Pit1, Pit2, BLVR, PAR1 (hRFT3) and PAR2 (hRFT1) in blood granulocytes of the subject compared to blood granulocytes of a healthy control subject is indicative of a granulocyte-related inflammatory state or an exacerbation of the granulocyte-related inflammatory state in rheumatoid arthritis.

2. The method according to claim 1, provided that when said at least one RBD is one RBD, said membrane receptor is not Glucose Transporter 1 (GLUT1).

3. The method according to claim 1, wherein said at least one soluble receptor-binding domain is a set of three to six soluble receptor-binding domains.

4. The method according to claim 1, wherein said at least one soluble receptor-binding domain is a set of three to six soluble receptor-binding domains, provided that at least one soluble receptor-binding domain of said set does not interact with GLUT1 membrane receptor.

5. The method according to claim 1, wherein said target granulocytes are neutrophils and said inflammatory state is cystic fibrosis.

6. The method according to claim 1, wherein said at least one soluble receptor-binding domain is a combination of two soluble receptor-binding domains.

7. The method according to claim 6, wherein
said combination is the combination of HTLV-2 RBD (SEQ ID NO: 28) and KoRV RBD (SEQ ID NO: 20), and
said membrane receptors are GLUT1 and Phosphate inorganic Transporter (PiT1) respectively.

8. The method according to claim 6, wherein said combination is the combination of PERVA RBD (SEQ ID NO: 21) and BLV RBD (SEQ ID NO: 30), and said membrane receptors are PERV-A Receptor (PAR) and a membrane receptor interacting with Bovine Leukaemia Virus (BLV) respectively.

9. The method according to claim 1, comprising the following steps:

(a) contacting the at least one soluble receptor-binding domain, optionally marked with a tag, with said target granulocytes of said subject mammal to form at last one complex, said at least one complex being constituted by said at least one soluble receptor-binding domain and at least one membrane receptor of said target granulocytes, (b) identifying said at least one complex formed, (c) quantifying the expression of each membrane receptor of said subject target granulocytes that form said complex, (d) conducting step (a) with target granulocytes of a control mammal and identifying said at least one complex formed as in step (b), and quantifying the expression of each membrane receptor of said control target granulocytes that form said complex as in step (c), and (e) comparing the level of expression of membrane receptors in step (c) and (d), an overexpression or underexpression of the membrane receptors of target granulocytes of said subject mammal compared with said control mammal indicating the inflammatory state.

10. The method of claim 9, wherein said control mammal is the same mammal species as the subject mammal.

11. The method of claim 10, wherein said granulocytes are neutrophils.

12. The method of claim 9, wherein the inflammatory state is cystic fibrosis.

13. The method of claim 12, comprising the following steps:

(a) contacting at least one of HTLV-2 RBD (SEQ ID NO: 28) and KoRV RBD (SEQ ID NO: 20), optionally marked with a tag, with lung neutrophils of the subject mammal to form the at least one complex, (b) identifying said at least one complex formed, said at least one complex being constituted by HTLV-2 RBD and GLUT1 membrane receptor, and/or KoRV RBD and Pill membrane receptor of said lung neutrophils, (c) quantifying the expression of said GLUT1 and/or Pill membrane receptor of said lung neutrophils that form said complex, (d) conducting step (a) with blood neutrophils of the subject mammal, and identifying and quantifying the expression of said GLUT1 and/or Pill membrane receptor of said blood neutrophils that form said complex as in steps (b) and (c), and (e) comparing the level of expression of each membrane receptor, an overexpression of GLUT1 and/or Pill in the lung neutrophils compared with the blood neutrophils indicating a pulmonary inflammatory state during cystic fibrosis.

14. The method of claim 12, comprising the following steps:

(a) contacting at least one of PERVA RBD (SEQ ID NO: 21) and BLV RBD (SEQ ID NO: 30), optionally marked with a tag, with lung neutrophils of the subject mammal to form the at least one complex, (b) identifying said at least one complex formed, said at least complex being constituted by PERVA RBD and PAR membrane receptor of said lung neutrophils, and/or BLV RBD and a membrane receptor interacting with BLV, (c) quantifying the expression of said PAR and/or said membrane receptor interacting with BLV of said lung neutrophils that form said complex, (d) conducting step (a) with blood neutrophils of the subject mammal, and identifying and quantifying the expression of said PAR and/or said membrane receptor interacting with BLV of said blood neutrophils that form said complex as in steps (b) and (c), and (e) comparing the level of expression of each membrane receptor, an overexpression of said membrane receptor interacting with BLV in the blood neutrophils compared with the lung neutrophils and/or an underexpression of PAR in the blood neutrophils compared with the lung neutrophils indicating a pulmonary inflammatory state during cystic fibrosis.

15. The method of claim 10, wherein said granulocytes are eosinophils.

16. The method of claim 10, wherein said granulocytes are basophils.

17. The method of claim 10, wherein said granulocytes are mast cells.

* * * * *